(12) United States Patent
Green et al.

(10) Patent No.: US 6,383,744 B1
(45) Date of Patent: May 7, 2002

(54) HUMAN CHECKPOINT KINASE

(75) Inventors: Stephen Green; Andrea Georgina King, both of Chesire (GB); Olga Bandman, Mountain View; Susan G. Stuart, Montara, both of CA (US)

(73) Assignee: Incyte Genomics, Inc., Palo Alto, CA (US)

( * ) Notice: Subject to any disclaimer, the term of this patent is extended or adjusted under 35 U.S.C. 154(b) by 0 days.

(21) Appl. No.: 09/113,785

(22) Filed: Jul. 10, 1998

(51) Int. Cl.[7] .............................. C12Q 1/68; C12N 9/12; C12N 1/20; C12N 15/00; C07H 21/04
(52) U.S. Cl. ..................... 435/6; 435/194; 435/252.3; 435/320.1; 435/325; 536/23.2; 536/23.1
(58) Field of Search ............................ 435/194, 320.1, 435/252.3, 325, 6; 536/23.2, 23.1

(56) References Cited

U.S. PATENT DOCUMENTS 6,218,109 B1 * 4/2001 Elledge et al. .................. 435/6

OTHER PUBLICATIONS

Flaggs et al., Curr. Biol., 7, 977–986, Dec. 1997.*
Hillier et al., genbank–est 109 database, Aceession No. N99369, Apr. 1996.*
Nezu et al., geseq32 database, Accession No. T38285, May 1997.*
Sanchez, Y. et al., "Conservation of the Chk1 Checkpoint Pathway in Mammals: Linkage of DNA Damage to Cdk Regulation Through Cdc25", Science, 277:1497–1501 (1997).
Flaggs, G.M. and A. Plug, "ATM–dependent interactions", Database TREMBL (Online) EMBL, Accession No. AF032874, Jan. 27, 1998.
Hanks, S.K. and T. Hunter, "The Eukaryotic Protein Kinase Superfamily," The Protein Kinase Facts Books, Academic Press, San Diego, CA, I:7–20 (1995).
Peng, C.Y. et al., "Mitotic and $G_2$ Checkpoint Control: Regulation of 14–3–3 Protein Binding by Phosphorylation of Cdc25C on Serine–216," Science, 277:1501–1505 (1997).

Greenblatt, M.S. et al., "Mutations in the p53 Tumor Suppressor Gene: Clues to Cancer Etiology and Molecular Pathogenesis," Cancer Res., 54:4855–4878 (1994).

Powell, S.N. et al., "Differential Sensitivity of $p53^{(-)}$ and $p53^{(+)}$ Cells to Caffeine–induced Radiosensitization and Override of $G_2$ Delay," Cancer Res., 55:1643–1648 (1995).

Walworth, N. et al., (Direct Submission), GenBank Sequence Database(Accession L13742), National Center for Biotechnology Information, National Library of Medicine, Bethesda, Maryland, 20894, (GI 311175; GI 311176), Oct. 19, 1995.

Walworth, N. et al., "Fission yeast chk1 protein kinase links the rad checkpoint pathway to cdc2," Nature, 363:368–371 (1993).

Sanchez, Y. et al., (Direct Submission), GenBank Sequence Database(Accession AF016582), National Center for Biotechnology Information, National Library of Medicine, Bethesda, Maryland, 20894, (GI 2367669), Sep. 9, 1997.

Sanchez, Y. et al., (Direct Submission), GenBank Sequence Database(Accession AF016583), National Center for Biotechnology Information, National Library of Medicine, Bethesda, Maryland, 20894, (GI 2367670; GI 2367671), Sep. 9, 1997.

Flaggs, G.M. and A. Plug, (Direct Submission), GenBank Sequence Database(Accession AF032874), National Center for Biotechnology Information, National Library of Medicine Bethesda, Maryland, 20894, (GI 2687579; GI 2687580), Dec. 15, 1997.

* cited by examiner

Primary Examiner—Rebecca E. Prouty
Assistant Examiner—M. Monshipouri
(74) Attorney, Agent, or Firm—Incyte Genomocs, Inc.

(57) ABSTRACT

The invention provides a human checkpoint kinase (hChk1) and polynucleotides which identify and encode hChk1. The invention also provides expression vectors, host cells, antibodies, agonists, and antagonists. The invention also provides methods for diagnosing, treating or preventing disorders associated with expression of hChk1.

12 Claims, 9 Drawing Sheets

Figure 3:
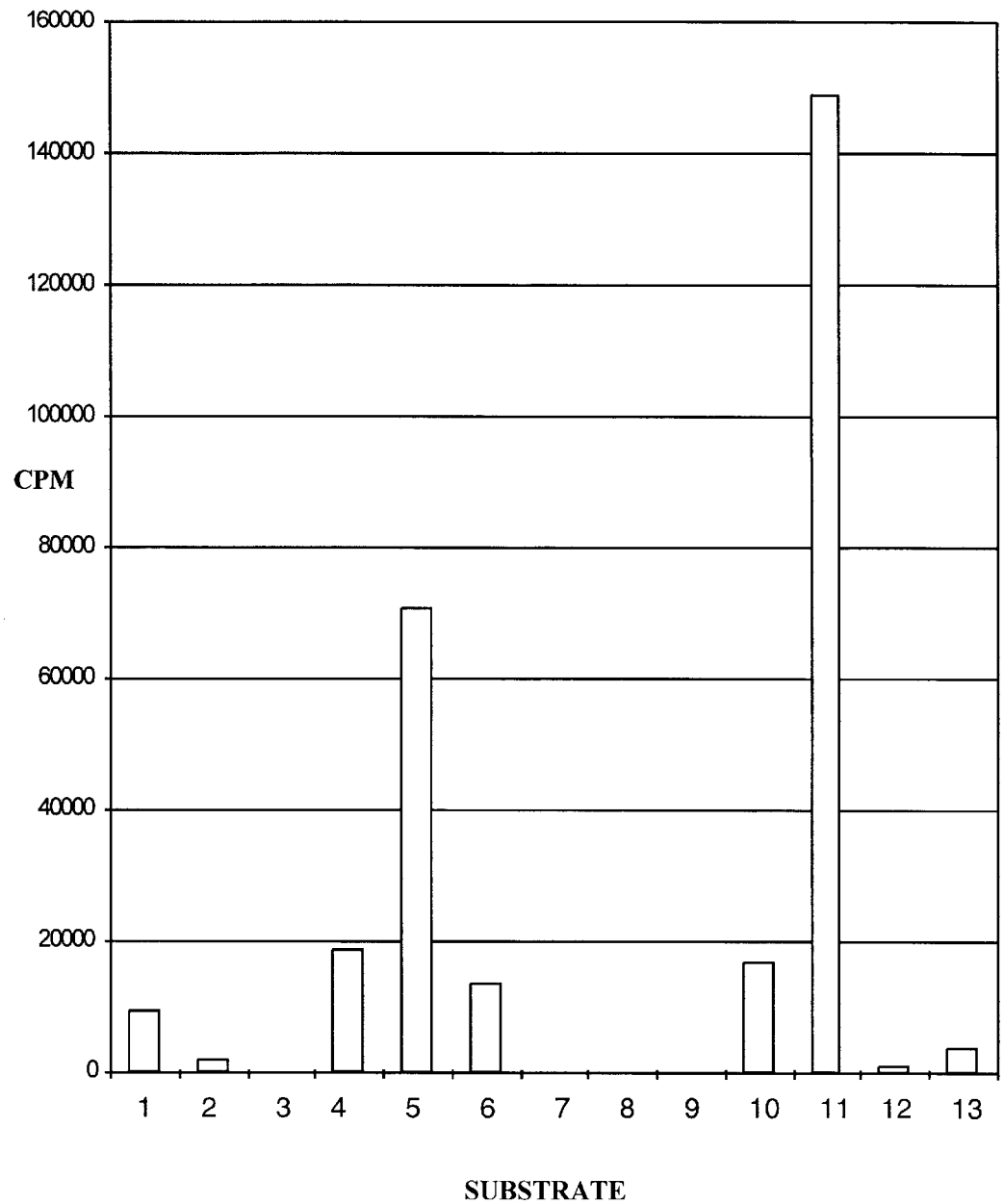

```
5' GAAT TCG GCT TCC ACC ATG GCA GTG CCC TTT GTG GAA GAC TGG GAC TTG GTG CAA
                   10          19          28          37          46          55
                              M   A   V   P   F   V   E   D   W   D   L   V   Q

ACC CTG GGA GAA GGT GCC TAT GGA GAA GTT CAA CTT GCT GTG AAT AGA GTA ACT
            64          73          82          91         100         109
 T   L   G   E   G   A   Y   G   E   V   Q   L   A   V   N   R   V   T

GAA GAA GCA GTC GCA GTG AAG ATT GTA GAT ATG AAG CGT GCC GTA GAC TGT CCA
           118         127         136         145         154         163
 E   E   A   V   A   V   K   I   V   D   M   K   R   A   V   D   C   P

GAA AAT ATT AAG AAA GAG ATC TGT AAT AAA ATG CTA AAT CAT GAA AAT GTA
           172         181         190         199         208         217
 E   N   I   K   K   E   I   C   N   K   M   L   N   H   E   N   V

GTA AAA TTC TAT GGT CAC AGG AGA GAA GGC AAT ATC CAA TAT TTA TTT CTG GAG
           226         235         244         253         262         271
 V   K   F   Y   G   H   R   R   E   G   N   I   Q   Y   L   F   L   E

TAC TGT AGT GGA GGA GAG CTT TTT GAC AGA ATA ATC GAG CCA GAC ATA GGC ATG CCT
           280         289         298         307         316         325
 Y   C   S   G   G   E   L   F   D   R   I   I   E   P   D   I   G   M   P

GAA CCA GAT GCT CAG AGA TTC TTC CAT CAA CTC ATG GCA GGG GTG GTT TAT CTG
           334         343         352         361         370         379
 E   P   D   A   Q   R   F   F   H   Q   L   M   A   G   V   V   Y   L

FIGURE 1A
```

```
        388              397        406            415            424            433
CAT GGT ATT GGA ATA ACT CAC AGG GAT ATT AAA CCA GAA AAT CTT CTG TTG GAT
 H   G   I   G   I   T   H   R   D   I   K   P   E   N   L   L   L   D 442              451        460            469            478            487
GAA AGG GAT AAC CTC AAA ATC TCA GAC TTT GCA ACA GTA TTT CGG TAT
 E   R   D   N   L   K   I   S   D   F   A   T   V   F   R   Y 496              505        514            523            532            541
AAT AAT CGT GAG CGT TTG TTG AAC AAG ATG TGT GGT ACT TTA CCA TAT GTT GCT
 N   N   R   E   R   L   L   N   K   M   C   G   T   L   P   Y   V   A 550              559        568            577            586            595
CCA GAA CTT CTG AAG AGA AGA GAA TTT CAT GCA ATG CTC GGA GAA CCA GTT GAT GTT TGG TCC
 P   E   L   L   K   R   R   E   F   H   A   M   L   G   E   P   V   D   V   W   S 604              613        622            631            640            649
TGT GGA ATA GTA CTT ACT GCA CTC ATG GCT GGA GAA TTG CCA GTT GAC CAA CCC
 C   G   I   V   L   T   A   L   M   A   G   E   L   P   V   D   Q   P 658              667        676            685            694            703
AGT GAC AGC TGT CAG GAG TAT TCT GAC TGG AAA GAA AAA ACA TAC CTC AAC
 S   D   S   C   Q   E   Y   S   D   W   K   E   K   T   Y   L   N 712              721        730            739            748            757
CCT TGG AAA AAA ATC GAT TCT GCT CCT CTA GCT CTG CAT AAA ATC TTA GTT
 P   W   K   K   I   D   S   A   P   L   A   L   H   K   I   L   V
```

FIGURE 1B

|  |  |  |  | 766 |  |  | 775 |  |  | 784 |  |  | 793 |  |  | 802 |  |  | 811 |
|---|---|---|---|---|---|---|---|---|---|---|---|---|---|---|---|---|---|---|---|
| GAG | AAT | CCA | TCA | GCA | AGA | ATT | ACC | ATT | CCA | GAC | ATC | AAA | AAA | GAT | AGA | TGG | TAC |
| E | N | P | S | A | R | I | T | I | P | D | I | K | K | D | R | W | Y |

|  |  |  |  | 820 |  |  | 829 |  |  | 838 |  |  | 847 |  |  | 856 |  |  | 865 |
|---|---|---|---|---|---|---|---|---|---|---|---|---|---|---|---|---|---|
| AAC | AAA | CCC | CTC | AAG | GGG | GCA | AAA | AGG | CCC | CGA | GTC | ACT | TCA | GGT | GTG |
| N | K | P | L | K | G | A | K | R | P | R | V | T | S | G | V |

|  |  |  |  | 874 |  |  | 883 |  |  | 892 |  |  | 901 |  |  | 910 |  |  | 919 |
|---|---|---|---|---|---|---|---|---|---|---|---|---|---|---|---|---|---|
| TCA | GAG | TCT | CCC | AGT | GGA | TTT | TCT | AAG | CAC | ATT | CAA | TCC | AAT | TTG | GAC | TTC | TCT |
| S | E | S | P | S | G | F | S | K | H | I | Q | S | N | L | D | F | S |

|  |  |  |  | 928 |  |  | 937 |  |  | 946 |  |  | 955 |  |  | 964 |  |  | 973 |
|---|---|---|---|---|---|---|---|---|---|---|---|---|---|---|---|---|---|
| CCA | GTA | AAC | AGT | GCT | TCT | AGT | GAA | AAT | GTG | AAG | TAC | TCC | AGT | TCT | CAG | CCA |
| P | V | N | S | A | S | S | E | N | V | K | Y | S | S | S | Q | P |

|  |  |  |  | 982 |  |  | 991 |  |  | 1000 |  |  | 1009 |  |  | 1018 |  |  | 1027 |
|---|---|---|---|---|---|---|---|---|---|---|---|---|---|---|---|---|---|
| GAA | CCC | CGC | ACA | GGT | CTT | TCC | TTA | TGG | GAT | ACC | AGC | CCC | TCA | TAC | ATT | GAT | AAA |
| E | P | R | T | G | L | S | L | W | D | T | S | P | S | Y | I | D | K |

|  |  |  |  | 1036 |  |  | 1045 |  |  | 1054 |  |  | 1063 |  |  | 1072 |  |  | 1081 |
|---|---|---|---|---|---|---|---|---|---|---|---|---|---|---|---|---|---|
| TTG | GTA | CAA | GGG | ATC | AGC | TTT | TCC | CAG | CCC | ACA | TGT | CCT | GAT | CAT | ATG | CTT | TTG |
| L | V | Q | G | I | S | F | S | Q | P | T | C | P | D | H | M | L | L |

|  |  |  |  | 1090 |  |  | 1099 |  |  | 1108 |  |  | 1117 |  |  | 1126 |  |  | 1135 |
|---|---|---|---|---|---|---|---|---|---|---|---|---|---|---|---|---|---|
| AAT | AGT | CAG | TTA | CTT | GGC | ACC | CCA | GGA | TCC | CAG | AAC | CCC | TCA | CAG | TGG | CGG | TTG |
| N | S | Q | L | L | G | T | P | G | S | Q | N | P | S | Q | W | R | L |

FIGURE1C

```
        1144         1153         1162         1171         1180         1189
GTC AAA AGA ATG ACA CGA TTC TTT ACC AAA TTG GAT GCA GAC AAA TCT TAT CAA
 V   K   R   M   T   R   F   F   T   K   L   D   A   D   K   S   Y   Q 1198         1207         1216         1225         1234         1243
TGC CTG AAA GAG ACT TGT GAG AAG TTG GGC TAT CAA TGG AAG AAA AGT TGT ATG
 C   L   K   E   T   C   E   K   L   G   Y   Q   W   K   K   S   C   M 1252         1261         1270         1279         1288         1297
AAT CAG GTT ACT ATA TCA ACA ACT GAT AGG AGA AAC AAT AAA CTC ATT TTC AAA
 N   Q   V   T   I   S   T   T   D   R   R   N   N   K   L   I   F   K 1306         1315         1324         1333         1342         1351
GTG AAT TTG TTA GAA ATG GAT GAT AAA ATA TTG GTT GAC TTC CGG CTT TCT AAG
 V   N   L   L   E   M   D   D   K   I   L   V   D   F   R   L   S   K 1360         1369         1378         1387         1396         1405
GGT GAT GGA TTG GAG TTC AAG AGA CAC TTC CTG AAG ATT AAA GGG AAG CTG ATT
 G   D   G   L   E   F   K   R   H   F   L   K   I   K   G   K   L   I 1414         1423         1432         1441         1450         1459
GAT ATT GTG AGC AGC CAG AAG GTT TGG CTT CCT GCC ACA TGA TCG GAC CAT CGG
 D   I   V   S   S   Q   K   V   W   L   P   A   T   *

1468         1477
CTC TGG GGA ATC CTC GAG TG 3'
```

FIGURE 1D

```
1    MAVPFVE-DWDLVQTLGEGAYGEVQLAVNR              516219
1    MAQKLDNFPYHIGREIGTGAFASVRLCYDD              GI 311176

30   VTEEAVAKIVDMKRAVDC---PENIK                  516219
31   -NAKIYAVKFVNKKHATSCMNAGVWARRMA              GI 311176

54   KEICINKM-LNHENVVKFYGHRREGNIQYL              516219
60   SEIQLHKLCNGHKNIIHFYNTAENPQWRWV              GI 311176

83   FLEYCSGGELFDRIEPDIGMPEPDAQRFFH              516219
90   VLEFAQGGDLFDKIEPDVGIDEDVAQFYFA              GI 311176

113  QLMAGVVYLHGIGITHRDIKPENLLDERD               516219
120  QLMEGISFMHSKGVAHRDLKPENILLDYNG              GI 311176

143  NLKISDFGLATVFRYNNRERLLNKMCGTLP              516219
150  NLKISDFGFASLFSYKGKSRLLNSPVGSPP              GI 311176
```

```
344  FSQPTCPDHMLLNSQLLGTPGSSQNPWQRL   516219
350  LNKNIDVTEILEKDPSLSQFCENEGFIKRL   GI 311176

374  VK----------RMTRFFTKLDADKS--    516219
380  AKKAKNFYEICPPERLTRFYSRASRETIID  GI 311176

390  --YQCLK--ETCEKLGYQWKKSCMNQVTIS  516219
410  HLYDSLRLLAISVTMKYVRNQTILY--VN   GI 311176

416  TTDRRNNKLIFKVNLLEMDDKI-LVDFRLS  516219
437  LHDKRKCLLQGVIELTNLGHNLELINFIKR  GI 311176

445  KGDGLEFKRHFLKIKGKLIDIVSSQKVWLP  516219
467  NGDPLEWRKFFKNVVSSIGKPIVLTDV--S  GI 311176

475  AT    516219
495  QN    GI 311176
```

FIGURE 2C

| Library | Lib Description | Library Abun | Library Pct Abun |
|---|---|---|---|
| CORNNOT01 | eye, corneal fibroblasts primary line, 76 | 1 | 0.1003 |
| TLYMTXP01 | T-lymphocyte, activated, TIGR | 1 | 0.0546 |
| THP1T7T01 | periph blood, promonocyte line, THP-1, AML, untreated | 1 | 0.0483 |
| OVARTUT03 | ovary tumor, seroanaplastic CA, 52F | 2 | 0.0471 |
| TLYJINT01 | Jurkat line, T-cell leukemia, M, t/PMA | 2 | 0.0453 |
| HNT2NOM02 | teratoCA line, hNT2, untreated, WM | 1 | 0.0391 |
| BRAIUNT01 | brain, neurogenic tumor line, SK-N-MC, neuroepithelioma, 14F | 1 | 0.0293 |
| OVARTUT02 | ovary tumor, mucinous cystadenoma, 51F | 1 | 0.0283 |
| HNT2TXT01 | teratoCA line, hNT2, t/mouse leptin, RA | 1 | 0.0279 |
| 293TF2T01 | kidney epithelial transf embryo line, 293-EBNA, t/5AZA | 1 | 0.0277 |
| LNODNOT08 | lymph node, peripancreatic, aw/pancreatic adenoCA, 65M | 1 | 0.0270 |
| SEMVNOT03 | seminal vesicle, aw/adenoCA, 56M | 1 | 0.0263 |
| COLNTUT16 | colon tumor, adenoCA, 60M, m/COLNNOT07/08/09/11 | 1 | 0.0256 |
| OVARTUT04 | ovary tumor, TC CA, 53F | 1 | 0.0252 |
| PANCNOT17 | pancreas, aw/neuroendocrine CA, 65F | 1 | 0.0246 |
| MMLR1DT01 | periph blood, macrophages, adher PBMC, M/F, 24-hr MLR | 1 | 0.0236 |
| COLNNOT16 | colon, sigmoid, aw/adenoCA, 62M, m/COLNTUT03 | 1 | 0.0208 |
| TESTTUT02 | testis tumor, embryonal CA, 31M | 1 | 0.0134 |
| LIVSFEM02 | liver/spleen, fetal, 20wM, NORM, WM | 5 | 0.0132 |
| UCMCL5T01 | umb cord blood, mononuclear cells, t/IL-5 | 1 | 0.0084 |
| ISLTNOT01 | pancreas, islet cells, pool | 1 | 0.0064 |

FIGURE 4

US 6,383,744 B1

HUMAN CHECKPOINT KINASE

FIELD OF THE INVENTION

This invention relates to nucleic acid and amino acid sequences of a human checkpoint kinase and to the use of these sequences in the diagnosis, treatment, and prevention of cancer and immune disorders.

BACKGROUND OF THE INVENTION

Kinases regulate many different processes such as cell proliferation, differentiation, and cell signaling by adding phosphate groups to proteins. Reversible protein phosphorylation is the main strategy for controlling activities of eukaryotic cells. It is estimated that more than 1000 of the 10,000 proteins active in a typical mammalian cell are phosphorylated. The high energy phosphate which drives this activation is generally transferred from adenosine triphosphate molecules (ATP) to a particular protein by protein kinases and removed from that protein by protein phosphatases. Phosphorylation occurs in response to extracellular signals, cell cycle checkpoints, and environmental or nutritional stresses. Protein kinases are roughly divided into two groups; those that phosphorylate tyrosine residues (protein tyrosine kinases, PTK) and those that phosphorylate serine or threonine residues (serine/threonine kinases, STK). A few protein kinases have dual specificity for serine/threonine and tyrosine residues.

Almost all kinases contain a similar 250–300 amino acid catalytic domain containing specific residues and sequence motifs characteristic of the kinase family. (Hardie, G. and Hanks, S. (1995) *The Protein Kinase Facts Books,* Vol I:7–20 Academic Press, San Diego, Calif.) In particular, two protein kinase signature sequences have been identified in the kinase domain, the first containing an active site lysine residue involved in ATP binding, and the second containing an aspartate residue important for catalytic activity. If a protein analyzed includes the two protein kinase signatures, the probability of that protein being a protein kinase is close to 100% (MOTIFS search program, Genetics Computer Group, Madison, Wis.)

In the process of cell division, the order and timing of cell cycle transitions is under control of cell cycle checkpoints, regulatory pathways which ensure that critical events such as DNA replication and chromosome segregation are carried out with precision. If DNA is damaged, e.g. by radiation, a checkpoint pathway is activated that arrests the cell cycle to provide time for repair. If the damage is extensive, apoptosis is induced. In the absence of such checkpoints, the damaged DNA is inherited by aberrant cells which may cause proliferative disorders such as cancer. Protein kinases play an important role in this process. For example, a specific kinase, checkpoint kinase 1 (Chk1), has been identified in yeast and mammals and is activated by DNA damage in yeast. Activation of Chk1 leads to the arrest of the cell at the G2/M transition. (Sanchez, Y. et al. (1997) Science 277:1497–1501.) Specifically, Chk1 phosphorylates the cell division cycle phosphatase CDC25, inhibiting its normal function which is to dephosphorylate and activate the cyclin-dependent kinase Cdc2. Cdc2 activation controls the entry of cells into mitosis. (Peng, C-Y et al. (1997) Science 277:1501–1505.) Thus, activation of Chk1 prevents the damaged cell from entering mitosis.

The regulation of cell cycle kinases, and in particular checkpoint kinase, has important implications for the control of proliferative diseases such as cancer. For example, in response to DNA damage in mammalian cells, the tumor suppressor p53 acts in a checkpoint pathway for cell cycle control by inducing the transcription of a cyclin-dependent kinase inhibitor resulting in G1/S arrest. (Sanchez et al., supra) p53-deficient cells with damaged DNA are unable to arrest in G1/S, a condition which can lead to cancer. It has been estimated that p53 may be non-functional in at least 60% of human cancers. (Greenblatt, M. S. et al. (1994) Cancer Research 54:4855–4878.) A similar deficiency in a checkpoint kinase, such as Chk1, may also contribute to cancer by failure to arrest cells with damaged DNA at other checkpoints such as G2/M.

Furthermore, it has been reported that in p53-deficient tumor cells, agents known to override G2/M arrest, specifically methylxanthines such as caffeine, induce a selective sensitization of these cells to agents which damage DNA (radiation or DNA cross-linking, chemotherapeutic agents). (Powell, S. N. et al. (1995) Cancer Research 55:1643–1648.) Thus, agents which can override G2/M arrest may be useful radiosensitizing or chemosensitizing agents for cancer treatment. Since Chk1 has been shown to induce G2/M arrest, Chk1 inhibitors may be useful in this regard.

The discovery of a new human checkpoint kinase and the polynucleotides encoding it satisfies a need in the art by providing new compositions which are useful in the diagnosis, treatment, and prevention of cancer and immune disorders.

SUMMARY OF THE INVENTION

The invention is based on the discovery of a new human checkpoint kinase (hChk1), the polynucleotides encoding hChk1, and the use of these compositions for the diagnosis, treatment, or prevention of cancer and immune disorders.

The invention features a substantially purified polypeptide comprising the amino acid sequence of SEQ ID NO:1 or a fragment of SEQ ID NO:1.

The invention further provides a substantially purified variant having at least 90% amino acid sequence identity to the amino acid sequence of SEQ ID NO:1 or a fragment of SEQ ID NO:1. The invention also provides an isolated and purified polynucleotide encoding the polypeptide comprising the sequence of SEQ ID NO:1 or a fragment of SEQ ID NO:1. The invention also includes an isolated and purified polynucleotide variant having at least 70% polynucleotide sequence identity to the polynucleotide encoding the polypeptide comprising the amino acid sequence of SEQ ID NO:1 or a fragment of SEQ ID NO:1. The invention further provides an isolated and purified polynucleotide comprising the polynucleotide sequence of SEQ ID NO:16, or a fragment of SEQ ID NO:16.

The invention further provides an isolated and purified polynucleotide which hybridizes under stringent conditions to the polynucleotide encoding the polypeptide comprising the amino acid sequence of SEQ ID NO:1 or a fragment of SEQ ID NO:1, as well as an isolated and purified polynucleotide which is complementary to the polynucleotide encoding the polypeptide comprising the amino acid sequence of SEQ ID NO:1 or a fragment of SEQ ID NO:1.

The invention also provides an isolated and purified polynucleotide comprising the polynucleotide sequence of SEQ ID NO:2 or a fragment of SEQ ID NO:2, and an isolated and purified polynucleotide variant having at least 70% polynucleotide sequence identity to the polynucleotide comprising the polynucleotide sequence of SEQ ID NO:2 or a fragment of SEQ ID NO:2. The invention also provides an isolated and purified polynucleotide having a sequence complementary to the polynucleotide comprising the polynucleotide sequence of SEQ ID NO:2 or a fragment of SEQ ID NO:2.

The invention further provides an expression vector comprising at least a fragment of the polynucleotide encoding the polypeptide comprising the sequence of SEQ ID NO:1 or a fragment of SEQ ID NO:1. In another aspect, the expression vector is contained within a host cell.

The invention also provides a method for producing a polypeptide, the method comprising the steps of: (a) culturing the host cell comprising an expression vector containing at least a fragment of a polynucleotide encoding the polypeptide comprising the amino acid sequence of SEQ ID NO:1 or a fragment of SEQ ID NO:1 under conditions suitable for the expression of the polypeptide; and (b) recovering the polypeptide from the host cell culture.

The invention also provides a pharmaceutical composition comprising a substantially purified polypeptide having the sequence of SEQ ID NO:1 or a fragment of SEQ ID NO:1 in conjunction with a suitable pharmaceutical carrier.

The invention further includes a purified antibody which binds to a polypeptide comprising the sequence of SEQ ID NO:1 or a fragment of SEQ ID NO:1, as well as a purified agonist and a purified antagonist or inhibitor of the polypeptide.

The invention also provides a method for treating or preventing a cancer, the method comprising administering to a subject in need of such treatment an effective amount of a pharmaceutical composition comprising a substantially purified polypeptide having the amino acid sequence of SEQ ID NO:1 or a fragment of SEQ ID NO:1.

The invention also provides a method for treating or preventing an immune disorder, the method comprising administering to a subject in need of such treatment an effective amount of a pharmaceutical composition comprising a substantially purified polypeptide having the amino acid sequence of SEQ ID NO:1 or a fragment of SEQ ID NO:1.

The invention also provides a method for treating a cancer, the method comprising administering to a subject in need of such treatment an effective amount of an antagonist or inhibitor of the polypeptide having the amino acid sequence of SEQ ID NO:1 or a fragment of SEQ ID NO:1, either alone or in combination with radiation or chemotherapy.

The invention also provides a method for detecting a polynucleotide in a sample containing nucleic acids, the method comprising the steps of: (a) hybridizing the complement of the polynucleotide encoding the polypeptide comprising the amino acid sequence of SEQ ID NO:1 or a fragment of SEQ ID NO:1 to at least one nucleic acid in the sample, thereby forming a hybridization complex; and (b) detecting the hybridization complex, wherein the presence of the hybridization complex correlates with the presence of a polynucleotide in the sample. In one aspect, this method further comprises amplifying the polynucleotide prior to hybridization.

BRIEF DESCRIPTION OF THE FIGURES AND TABLES

FIGS. 1A, 1B, 1C, and 1D show the amino acid sequence (SEQ ID NO:1) and nucleic acid sequence (SEQ ID NO:2) of hChk1. The alignment was produced using MacDNASIS PRO™ software (Hitachi Software Engineering Co. Ltd., San Bruno, Calif.).

FIGS. 2A, 2B, and 2C show the amino acid sequence alignments between hChk1 (516219; SEQ ID NO:1), and checkpoint kinase, Chk1 from yeast (GI 311176; SEQ ID NO:3), produced using the multisequence alignment program of LASERGENE™ software (DNASTAR Inc, Madison Wis.).

FIG. 3 shows the kinase activity of purified hChk1 in vitro against various natural and synthetic substrates. The Y axis represents radioactivity (cpm) incorporated into phosphorylated products, and the X axis, various synthetic peptide substrates as follows: (1) mylein basic protein (MBP), (2) casein, (3) phosviotin, (4) poly (Arg, Pro, Thr) 6:3:1, (5) poly (Arg, Ser) 3:1, (6) poly (Arg, Pro, Thr) 1:1:1, (7) MBP fragment, (8) cAMP substrate 1 (RRKASGP), (9) cAMP substrate 2 (GRGLSLSR), (10) protein kinase C substrate, (11) calmodulin substrate, (12) Kemptide, (13) cAMP substrate 3 (LRRWSLG).

FIG. 4 shows the northern analysis for the nucleotide sequence (SEQ ID NO:2) of hChk1 produced electronically using the LIFESEQ™ database (Incyte Pharmaceuticals, Palo Alto Calif.).

Table 1 shows the programs/algorithms, descriptions, references and threshold parameters used to identify and characterize hChk1.

DESCRIPTION OF THE INVENTION

Before the present proteins, nucleotide sequences, and methods are described, it is understood that this invention is not limited to the particular methodology, protocols, cell lines, vectors, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a," "an," and "the" include plural reference unless the context clearly dictates otherwise. Thus, for example, a reference to "a host cell" includes a plurality of such host cells, and a reference to "an antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are cited for the purpose of describing and disclosing the cell lines, vectors, and methodologies which are reported in the publications and which might be used in connection with the invention. Nothing herein is to be construed as an admission that the invention is not entitled to antedate such disclosure by virtue of prior invention.

Definitions

"hChk1," as used herein, refers to the amino acid sequences of substantially purified hChk1 obtained from any species, particularly a mammalian species, including bovine, ovine, porcine, murine, equine, and preferably the human species, from any source, whether natural, synthetic, semi-synthetic, or recombinant.

The term "agonist," as used herein, refers to a molecule which, when bound to hChk1, increases or prolongs the duration of the effect of hChk1. Agonists may include proteins, nucleic acids, carbohydrates, or any other molecules which bind to and modulate the effect of hChk1.

An "allelic variant," as this term is used herein, is an alternative form of the gene encoding hChk1. Allelic variants may result from at least one mutation in the nucleic acid sequence and may result in altered mRNAs or in polypeptides whose structure or function may or may not be altered. Any given natural or recombinant gene may have none, one, or many allelic forms. Common mutational changes which give rise to allelic variants are generally ascribed to natural deletions, additions, or substitutions of nucleotides. Each of these types of changes may occur alone, or in combination with the others, one or more times in a given sequence.

"Altered" nucleic acid sequences encoding hChk1, as described herein, include those sequences with deletions, insertions, or substitutions of different nucleotides, resulting in a polynucleotide the same as hChk1 or a polypeptide with at least one functional characteristic of hChkl. Included within this definition are polymorphisms which may or may not be readily detectable using a particular oligonucleotide probe of the polynucleotide encoding hChk1, and improper or unexpected hybridization to allelic variants, with a locus other than the normal chromosomal locus for the polynucleotide sequence encoding hChk1. The encoded protein may also be "altered," and may contain deletions, insertions, or substitutions of amino acid residues which produce a silent change and result in a functionally equivalent hChk1. Deliberate amino acid substitutions may be made on the basis of similarity in polarity, charge, solubility, hydrophobicity, hydrophilicity, and/or the amphipathic nature of the residues, as long as the biological or immunological activity of hChk1 is retained. For example, negatively charged amino acids may include aspartic acid and glutamic acid, positively charged amino acids may include lysine and arginine, and amino acids with uncharged polar head groups having similar hydrophilicity values may include leucine, isoleucine, and valine; glycine and alanine; asparagine and glutamine; serine and threonine; and phenylalanine and tyrosine.

The terms "amino acid" or "amino acid sequence," as used herein, refer to an oligopeptide, peptide, polypeptide, or protein sequence, or a fragment of any of these, and to naturally occurring or synthetic molecules. In this context, "fragments," "immunogenic fragments," or "antigenic fragments" refer to fragments of hChk1 which are preferably at least 5 to about 15 amino acids in length, most preferably at least 14 amino acids, and which retain some biological activity or immunological activity of hChk1. Where "amino acid sequence" is recited herein to refer to an amino acid sequence of a naturally occurring protein molecule, "amino acid sequence" and like terms are not meant to limit the amino acid sequence to the complete native amino acid sequence associated with the recited protein molecule.

"Amplification," as used herein, relates to the production of additional copies of a nucleic acid sequence. Amplification is generally carried out using polymerase chain reaction (PCR) technologies well known in the art. (See, e.g., Dieffenbach, C. W. and G. S. Dveksler (1995) *PCR Primer, a Laboratory Manual,* Cold Spring Harbor Press, Plainview, N.Y., pp.1–5.)

The term "antagonist," as it is used herein, refers to a molecule which, when bound to hChk1, decreases or prevents the activity or effect of hChk1. Antagonists may include proteins, nucleic acids, carbohydrates, antibodies, organic molecules (whether naturally occuring, semisynthetic or totally synthetic), or any other molecules which bind to and modulate the effect of hChk1.

As used herein, the term "antibody" refers to intact molecules as well as to fragments thereof, such as Fab, F(ab')$_2$, and Fv fragments, which are capable of binding the epitopic determinant. Antibodies that bind hChk1 polypeptides can be prepared using intact polypeptides or using fragments containing small peptides of interest as the immunizing antigen. The polypeptide or oligopeptide used to immunize an animal (e.g., a mouse, a rat, or a rabbit) can be derived from the translation of RNA, or synthesized chemically, and can be conjugated to a carrier protein if desired. Commonly used carriers that are chemically coupled to peptides include bovine serum albumin, thyroglobulin, and keyhole limpet hemocyanin (KLH). The coupled peptide is then used to immunize the animal.

The term "antigenic determinant," as used herein, refers to that fragment of a molecule (i.e., an epitope) that makes contact with a particular antibody. When a protein or a fragment of a protein is used to immunize a host animal, numerous regions of the protein may induce the production of antibodies which bind specifically to antigenic determinants (given regions or three-dimensional structures on the protein). An antigenic determinant may compete with the intact antigen (i.e., the immunogen used to elicit the immune response) for binding to an antibody.

The term "antisense," as used herein, refers to any composition containing a nucleic acid sequence which is complementary to the "sense" strand of a specific nucleic acid sequence. Antisense molecules may be produced by any method including synthesis or transcription. Once introduced into a cell, the complementary nucleotides combine with natural sequences produced by the cell to form duplexes and to block either transcription or translation. The designation "negative" can refer to the antisense strand, and the designation "positive" can refer to the sense strand.

As used herein, the term "biologically active," refers to a protein having structural, regulatory, or biochemical functions of a naturally occurring molecule. Likewise, "immunologically active" refers to the capability of the natural, recombinant, or synthetic hChk1, or of any oligopeptide thereof, to induce a specific immune response in appropriate animals or cells and to bind with specific antibodies.

The terms "complementary" or "complementarity," as used herein, refer to the natural binding of polynucleotides by base pairing. For example, the sequence "5' A-G-T 3'" binds to the complementary sequence "3' T-C-A 5'." Complementarity between two single-stranded molecules may be "partial," such that only some of the nucleic acids bind, or it may be "complete," such that total complementarity exists between the single stranded molecules. The degree of complementarity between nucleic acid strands has significant effects on the efficiency and strength of the hybridization between the nucleic acid strands. This is of particular importance in amplification reactions, which depend upon binding between nucleic acids strands, and in the design and use of peptide nucleic acid (PNA) molecules.

A "composition comprising a given polynucleotide sequence" or a "composition comprising a given amino acid sequence," as these terms are used herein, refer broadly to any composition containing the given polynucleotide or amino acid sequence. The composition may comprise a dry formulation or an aqueous solution. Compositions comprising polynucleotide sequences encoding hChk1 or fragments of hChk1 may be employed as hybridization probes. The probes may be stored in freeze-dried form and may be associated with a stabilizing agent such as a carbohydrate. In hybridizations, the probe may be deployed in an aqueous solution containing salts, e.g., NaCl, detergents, e.g.,sodium dodecyl sulfate (SDS), and other components, e.g., Denhardt's solution, dry milk, salmon sperm DNA, etc.

"Consensus sequence," as used herein, refers to a nucleic acid sequence which has been resequenced to resolve uncalled bases, extended using XL-PCR™ (Perkin Elmer, Norwalk, Conn.) in the 5' and/or the 3' direction, and resequenced, or which has been assembled from the overlapping sequences of more than one Incyte Clone using a computer program for fragment assembly, such as the GEL VIEW™ Fragment Assembly system (GCG, Madison, Wis.). Some sequences have been both extended and assembled to produce the consensus sequence.

As used herein, the term "correlates with expression of a polynucleotide" indicates that the detection of the presence of nucleic acids, the same or related to a nucleic acid sequence encoding hChk1, by Northern analysis is indicative of the presence of nucleic acids encoding hChk1 in a sample, and thereby correlates with expression of the transcript from the polynucleotide encoding hChk1.

A "deletion," as the term is used herein, refers to a change in the amino acid or nucleotide sequence that results in the absence of one or more amino acid residues or nucleotides.

The term "derivative," as used herein, refers to the chemical modification of a polypeptide sequence, or a polynucleotide sequence. Chemical modifications of a polynucleotide sequence can include, for example, replacement of hydrogen by an alkyl, acyl, or amino group. A derivative polynucleotide encodes a polypeptide which retains at least one biological or immunological function of the natural molecule. A derivative polypeptide is one modified by glycosylation, pegylation, or any similar process that retains at least one biological or immunological function of the polypeptide from which it was derived.

The term "similarity," as used herein, refers to a degree of complementarity. There may be partial similarity or complete similarity. The word "identity" may substitute for the word "similarity." A partially complementary sequence that at least partially inhibits an identical sequence from hybridizing to a target nucleic acid is referred to as "substantially similar." The inhibition of hybridization of the completely complementary sequence to the target sequence may be examined using a hybridization assay (Southern or Northern blot, solution hybridization, and the like) under conditions of reduced stringency. A substantially similar sequence or hybridization probe will compete for and inhibit the binding of a completely similar (identical) sequence to the target sequence under conditions of reduced stringency. This is not to say that conditions of reduced stringency are such that non-specific binding is permitted, as reduced stringency conditions require that the binding of two sequences to one another be a specific (i.e., a selective) interaction. The absence of non-specific binding may be tested by the use of a second target sequence which lacks even a partial degree of complementarity (e.g., less than about 30% similarity or identity). In the absence of non-specific binding, the substantially similar sequence or probe will not hybridize to the second non-complementary target sequence.

The phrases "percent identity" or "% identity" refer to the percentage of sequence similarity found in a comparison of two or more amino acid or nucleic acid sequences. Percent identity can be determined electronically, e.g., by using the MegAlign™ program (DNASTAR, Inc., Madison Wis.). The MegAlign™ program can create alignments between two or more sequences according to different methods, e.g., the clustal method. (See, e.g., Higgins, D. G. and P. M. Sharp (1988) Gene 73:237–244.) The clustal algorithm groups sequences into clusters by examining the distances between all pairs. The clusters are aligned pairwise and then in groups. The percentage similarity between two amino acid sequences, e.g., sequence A and sequence B, is calculated by dividing the length of sequence A, minus the number of gap residues in sequence A, minus the number of gap residues in sequence B, into the sum of the residue matches between sequence A and sequence B, times one hundred. Gaps of low or of no similarity between the two amino acid sequences are not included in determining percentage similarity. Percent identity between nucleic acid sequences can also be counted or calculated by other methods known in the art, e.g., the Jotun Hein method. (See, e.g., Hein, J. (1990) Methods Enzymol. 183:626–645.) Identity between sequences can also be determined by other methods known in the art, e.g., by varying hybridization conditions.

"Human artificial chromosomes" (HACs), as described herein, are linear microchromosomes which may contain DNA sequences of about 6 kb to 10 Mb in size, and which contain all of the elements required for stable mitotic chromosome segregation and maintenance. (See, e.g., Harrington, J. J. et al. (1997) Nat Genet. 15:345–355.)

The term "humanized antibody," as used herein, refers to antibody molecules in which the amino acid sequence in the non-antigen binding regions has been altered so that the antibody more closely resembles a human antibody, and still retains its original binding ability.

"Hybridization," as the term is used herein, refers to any process by which a strand of nucleic acid binds with a complementary strand through base pairing.

As used herein, the term "hybridization complex" refers to a complex formed between two nucleic acid sequences by virtue of the formation of hydrogen bonds between complementary bases. A hybridization complex may be formed in solution (e.g., $C_0t$ or $R_0t$ analysis) or formed between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

The words "insertion" or "addition," as used herein, refer to changes in an amino acid or nucleotide sequence resulting in the addition of one or more amino acid residues or nucleotides, respectively, to the sequence found in the naturally occurring molecule.

"Immune response" can refer to conditions associated with inflammation, trauma, immune disorders, or infectious or genetic disease, etc. These conditions can be characterized by expression of various factors, e.g., cytokines, chemokines, and other signaling molecules, which may affect cellular and systemic defense systems.

The term "microarray," as used herein, refers to an arrangement of distinct polynucleotides arrayed on a substrate, e.g., paper, nylon or any other type of membrane, filter, chip, glass slide, or any other suitable solid support.

The terms "element" or "array element" as used herein in a microarray context, refer to hybridizable polynucleotides arranged on the surface of a substrate.

The term "modulate," as it appears herein, refers to a change in the activity of hChk1. For example, modulation may cause an increase or a decrease in protein activity, binding characteristics, or any other biological, functional, or immunological properties of hChk1.

The phrases "nucleic acid" or "nucleic acid sequence," as used herein, refer to a nucleotide, oligonucleotide, polynucleotide, or any fragment thereof. These phrases also refer to DNA or RNA of genomic or synthetic origin which may be single-stranded or double-stranded and may represent the sense or the antisense strand, to peptide nucleic acid (PNA), or to any DNA-like or RNA-like material. In this context, "fragments" refers to those nucleic acid sequences which, when translated, would produce polypeptides retaining some functional characteristic, e.g., antigenicity, or structural domain characteristic, e.g., ATP-binding site, of the full-length polypeptide.

The terms "operably associated" or "operably linked," as used herein, refer to functionally related nucleic acid sequences. A promoter is operably associated or operably linked with a coding sequence if the promoter controls the translation of the encoded polypeptide. While operably associated or operably linked nucleic acid sequences can be contiguous and in the same reading frame, certain genetic elements, e.g., repressor genes, are not contiguously linked to the sequence encoding the polypeptide but still bind to operator sequences that control expression of the polypeptide.

The term "oligonucleotide," as used herein, refers to a nucleic acid sequence of at least about 6 nucleotides to 60 nucleotides, preferably about 15 to 30 nucleotides, and most preferably about 20 to 25 nucleotides, which can be used in PCR amplification or in a hybridization assay or microarray. As used herein, the term "oligonucleotide" is substantially equivalent to the terms "amplimer," "primer," "oligomer," and "probe," as these terms are commonly defined in the art.

"Peptide nucleic acid" (PNA), as used herein, refers to an antisense molecule or anti-gene agent which comprises an oligonucleotide of at least about 5 nucleotides in length linked to a peptide backbone of amino acid residues ending in lysine. The terminal lysine confers solubility to the composition. PNAs preferentially bind complementary single stranded DNA or RNA and stop transcript elongation, and may be pegylated to extend their lifespan in the cell. (See, e.g., Nielsen, P. E. et al. (1993) Anticancer Drug Des. 8:53–63.)

The term "sample," as used herein, is used in its broadest sense. A biological sample suspected of containing nucleic acids encoding hChk1, or fragments thereof, or hChk1 itself, may comprise a bodily fluid; an extract from a cell, chromosome, organelle, or membrane isolated from a cell; a cell; genomic DNA, RNA, or cDNA, in solution or bound to a solid support; a tissue; a tissue print; etc.

As used herein, the terms "specific binding" or "specifically binding" refer to that interaction between a protein or peptide and an agonist, an antibody, or an antagonist. The interaction is dependent upon the presence of a particular structure of the protein, e.g., the antigenic determinant or epitope, recognized by the binding molecule. For example, if an antibody is specific for epitope "A," the presence of a polypeptide containing the epitope A, or the presence of free unlabeled A, in a reaction containing free labeled A and the antibody will reduce the amount of labeled A that binds to the antibody.

As used herein, the term "stringent conditions" refers to conditions which permit hybridization between polynucleotides and the claimed polynucleotides. Stringent conditions can be defined by salt concentration, the concentration of organic solvent, e.g., formamide, temperature, and other conditions well known in the art. In particular, stringency can be increased by reducing the concentration of salt, increasing the concentration of formamide, or raising the hybridization temperature.

The term "substantially purified," as used herein, refers to nucleic acid or amino acid sequences that are removed from their natural environment and are isolated or separated, and are at least about 60% free, preferably about 75% free, and most preferably about 90% free from other components with which they are naturally associated.

A "substitution," as used herein, refers to the replacement of one or more amino acids or nucleotides by different amino acids or nucleotides, respectively.

"Transformation," as defined herein, describes a process by which exogenous DNA enters and changes a recipient cell. Transformation may occur under natural or artificial conditions according to various methods well known in the art, and may rely on any known method for the insertion of foreign nucleic acid sequences into a prokaryotic or eukaryotic host cell. The method for transformation is selected based on the type of host cell being transformed and may include, but is not limited to, viral infection, electroporation, heat shock, lipofection, and particle bombardment. The term "transformed" cells includes stably transformed cells in which the inserted DNA is capable of replication either as an autonomously replicating plasmid or as part of the host chromosome, as well as transiently transformed cells which express the inserted DNA or RNA for limited periods of time.

A "variant" of hChk1 polypeptides, as used herein, refers to an amino acid sequence that is altered by one or more amino acid residues. The variant may have "conservative" changes, wherein a substituted amino acid has similar structural or chemical properties (e.g., replacement of leucine with isoleucine). More rarely, a variant may have "nonconservative" changes (e.g., replacement of glycine with tryptophan). Analogous minor variations may also include amino acid deletions or insertions, or both. Guidance in determining which amino acid residues may be substituted, inserted, or deleted without abolishing biological or immunological activity may be found using computer programs well known in the art, for example, LASERGENE™ software.

The term "variant," when used in the context of a polynucleotide sequence, may encompass a polynucleotide sequence related to hChk1. This definition may also include, for example, "allelic" (as defined above), "splice," "species," or "polymorphic" variants. A splice variant may have significant identity to a reference molecule, but will generally have a greater or lesser number of polynucleotides due to alternate splicing of exons during mRNA processing. The corresponding polypeptide may possess additional functional domains or an absence of domains. Species variants are polynucleotide sequences that vary from one species to another. The resulting polypeptides generally will have significant amino acid identity relative to each other. A polymorphic variant is a variation in the polynucleotide sequence of a particular gene between individuals of a given species. Polymorphic variants also may encompass "single nucleotide polymorphisms" (SNPs) in which the polynucleotide sequence varies by one base. The presence of SNPs may be indicative of, for example, a certain population, a disease state, or a propensity for a disease state.

The Invention

The invention is based on the discovery of a new human checkpoint kinase (hChk1), the polynucleotides encoding hChk1, and the use of these compositions for the diagnosis, treatment, or prevention of cancer and immune disorders.

Nucleic acids encoding the hChk1 of the present invention were first identified in Incyte Clones 516219 from the mononuclear cell cDNA library (MMLR1DT01) and 2044650 from the promonocyte cell cDNA library (THP1T7T01) using a computer search, e.g., BLAST, for amino acid sequence alignments. A consensus sequence, SEQ ID NO:2, was derived from the following overlapping and/or extended nucleic acid sequences: Incyte Clones 046081H1, 046081F1 and 046081X3 (CORNNOT01), 516219H1, 516219F1 and 516219X5 (MMLR1DT01) 2044650H1 (THP1T7T01) and 2731758H1 (OVARTUT04); SEQ ID Nos: 4–11, respectively.

In one embodiment, the invention encompasses a polypeptide comprising the amino acid sequence of SEQ ID NO:1, as shown in FIGS. 1A, 1B, 1C, and 1D. hChk1 is 476 amino acids in length and has potential phosphorylation sites for cAMP- and cGMP-dependent protein kinase as at residue T378, for casein kinase II at T14, S88, T127, S214, T255, S296, S307, S317, S326, S333, T348, T382, S415, and S444, for protein kinase C at T127, S251, T417, and S468, and for tyrosine kinase at Y390 and Y402. hChk1 has two signature sequences for protein kinases located between residues L15 and K38 and residues I126 and L138. The first sequence is located in subdomain I of the potential kinase domain and contains the characteristic motif, GXGXXGXV, between residues G16 and V21, and the ATP-binding residue, K38. The second sequence located in subdomain VI contains the consensus motif HRDLKXXN with a conservative substitution of I for L at residue 131, and the important aspartic acid, catalytic active site residue, D130. As shown in FIGS. 2A, 2B, and 2C, hChk1 has chemical and structural similarity with checkpoint kinase from yeast, Chk1 (GI 311176; SEQ ID NO:3). In particular, hChk1 and Chk1 share 23% identity. The two proteins share the consensus motif GXGXXGXV in subdomain I, the ATP-binding residue at K38, the consensus motif HRDLKXXN in subdomain VI, and the catalytic active site residue, D130.

The nucleotide sequence encoding hChk1 was expressed in insect cells using a baculovirus vector and hChk1 was isolated and prepared for protein activity assays. The expression of the protein was assessed by western analysis using an antibody prepared against a C-terminal portion of the polypeptide (CGKIKGKLIDIVSSQKVWLPAT; SEQ ID NO:12). FIG. 3 shows the results of an in vitro protein kinase phosphorylation assay using hChk1 incubated with various proteins or synthetic peptide substrates and [γ-$^{33}$P] ATP as the phosphate donor. Control reactions were carried out in the absence of hChk1. hChk1 showed the highest phosphorylating activity using a calmodulin substrate or the synthetic peptide substrate, poly (Arg, Ser) 3:1, but significant activity was also found with mylein basic protein (MBP), casein, poly (Arg, Pro, Thr) 6:3:1, protein kinase C (PKC) substrate, and cAMP substrate.

Electronic northern analysis (FIG. 4) using the LIFESEQ™ database showed the expression of this sequence in various libraries, at least 67% of which are immortalized or cancerous and at least 38% of which involve immune response. Of particular note is the expression of hChk1 in cancers of the brain, ovaries, lymph nodes, colon, testis, and leukemia.

The invention also encompasses hChk1 variants. A preferred hChk1 variant is one which has at least about 80%, more preferably at least about 90%, and most preferably at least about 95% amino acid sequence identity to the hChk1 amino acid sequence, and which contains at least one functional or structural characteristic of hChk1.

The invention also encompasses polynucleotides which encode hChk1. In a particular embodiment, the invention encompasses a polynucleotide sequence comprising the sequence of SEQ ID NO:2, which encodes an hChk1.

The invention also encompasses a variant of a polynucleotide sequence encoding hChk1. In particular, such a variant polynucleotide sequence will have at least about 70%, more preferably at least about 85%, and most preferably at least about 95% polynucleotide sequence identity to the polynucleotide sequence encoding hChk1. A particular aspect of the invention encompasses a variant of SEQ ID NO:2 which has at least about 70%, more preferably at least about 85%, and most preferably at least about 95% polynucleotide sequence identity to SEQ ID NO:2. Any one of the polynucleotide variants described above can encode an amino acid sequence which contains at least one functional or structural characteristic of hChk1.

It will be appreciated by those skilled in the art that as a result of the degeneracy of the genetic code, a multitude of polynucleotide sequences encoding hChk1, some bearing minimal similarity to the polynucleotide sequences of any known and naturally occurring gene, may be produced. Thus, the invention contemplates each and every possible variation of polynucleotide sequence that could be made by selecting combinations based on possible codon choices. These combinations are made in accordance with the standard triplet genetic code as applied to the polynucleotide sequence of naturally occurring hChk1, and all such variations are to be considered as being specifically disclosed.

Although nucleotide sequences which encode hChk1 and its variants are preferably capable of hybridizing to the nucleotide sequence of the naturally occurring hChk1 under appropriately selected conditions of stringency, it may be advantageous to produce nucleotide sequences encoding hChk1 or its derivatives possessing a substantially different codon usage, e.g., inclusion of non-naturally occurring codons. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding hChk1 and its derivatives without altering the encoded amino acid sequences include the production of RNA transcripts having more desirable properties, such as a greater half-life, than transcripts produced from the naturally occurring sequence.

The invention also encompasses production of DNA sequences which encode hChk1 and hChk1 derivatives, or fragments thereof, entirely by synthetic chemistry. After production, the synthetic sequence may be inserted into any of the many available expression vectors and cell systems using reagents well known in the art. Moreover, synthetic chemistry may be used to introduce mutations into a sequence encoding hChk1 or any fragment thereof.

Also encompassed by the invention are polynucleotide sequences that are capable of hybridizing to the claimed polynucleotide sequences, and, in particular, to that shown in SEQ ID NO:2, or a fragment of SEQ ID NO:2, under various conditions of stringency. (See, e.g., Wahl, G. M. and S. L. Berger (1987) Methods Enzymol. 152:399-407; Kimmel, A. R. (1987) Methods Enzymol. 152:507–511.) For example, stringent salt concentration will ordinarily be less than about 750 mM NaCl and 75 mM trisodium citrate, preferably less than about 500 mM NaCl and 50 mM trisodium citrate, and most preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and most preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100µg/ml denatured salmon sperm DNA (ssDNA). In a most preferred embodiment, hybridization will occur at 42° C. in 250 mM NaCl, 25 mM trisodium citrate, 1% SDS, 50 % formamide, and 200 µg/ml ssDNA. Useful variations on these conditions will be readily apparent to those skilled in the art.

The washing steps which follow hybridization can also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include temperature of at least about 25° C., more preferably of at least about 42° C., and most preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a most preferred embodiment, wash steps will occur at 68° C. in 15 mM NaCl, 1.5 mM trisodium citrate, and 0.1% SDS. Additional variations on these conditions will be readily apparent to those skilled in the art.

Methods for DNA sequencing are well known in the art and may be used to practice any of the embodiments of the invention. The methods may employ such enzymes as the Klenow fragment of DNA polymerase I, SEQUENASE® (US Biochemical Corp., Cleveland, Ohio), Taq polymerase (Perkin Elmer), thermostable T7 polymerase (Amersham, Chicago, Ill.), or combinations of polymerases and proofreading exonucleases such as those found in the ELONGASE™ Amplification System (GIBCO BRL, Gaithersburg, Md.). Preferably, sequence preparation is automated with machines such as the Hamilton Micro Lab 2200 (Hamilton, Reno, Nev.), Peltier Thermal Cycler (PTC200; MJ Research, Watertown, Mass.) and the ABI Catalyst 800 (Perkin Elmer). Sequencing is then carried out using either ABI 373 or 377 DNA Sequencing Systems (Perkin Elmer) or capillary electrophoresis (Molecular Dynamics). The resulting sequences are analyzed using a variety of alogrithms which are well known in the art. (See, e.g., Ausubel, supra, ch. 7.7; and Meyers, R. A. (1995) *Molecular Biology and Biotechnology*, Wiley VCH, Inc., New York, N.Y., pp. 856–853.)

The nucleic acid sequences encoding hChk1 may be extended utilizing a partial nucleotide sequence and employing various PCR-based methods known in the art to detect upstream sequences, such as promoters and regulatory elements. For example, one method which may be employed, restriction-site PCR, uses universal and nested primers to amplify unknown sequence from genomic DNA within a cloning vector. (See, e.g., Sarkar, G. (1993) PCR Methods Applic. 2:318–322.) Another method, inverse PCR, uses primers that extend in divergent directions to amplify unknown sequence from a circularized template. The template is derived from restriction fragments comprising a known genomic locus and surrounding sequences. (See, e.g., Triglia, T. et al. (1988) Nucleic Acids Res. 16:8186.) A third method, capture PCR, involves PCR amplification of DNA fragments adjacent to known sequences in human and yeast artificial chromosome DNA. (See, e.g., Lagerstrom, M. et al. (1991) PCR Methods Applic. 1:111–119.) In this method, multiple restriction enzyme digestions and ligations may be used to insert an engineered double-stranded sequence into a region of unknown sequence before performing PCR. Other methods which may be used to retrieve unknown sequences are known in the art. (See, e.g., Parker, J. D. et al. (1991) Nucleic Acids Res. 19:3055–306). Additionally, one may use PCR, nested primers, and PromoterFinder™ libraries to walk genomic DNA (Clontech, Palo Alto, Calif.). This procedure avoids the need to screen libraries and is useful in finding intron/exon junctions. For all PCR-based methods, primers may be designed using commercially available software, such as OLIGO™ 4.06 Primer Analysis software (National Biosciences Inc., Plymouth, Minn.) or another appropriate program, to be about 22 to 30 nucleotides in length, to have a GC content of about 50% or more, and to anneal to the template at temperatures of about 68° C. to 72° C.

When screening for full-length cDNAs, it is preferable to use libraries that have been size-selected to include larger cDNAs. In addition, random-primed libraries, which often include sequences containing the 5' regions of genes, are preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different nucleotide-specific, laser-stimulated fluorescent dyes, and a charge coupled device camera for detection of the emitted wavelengths. Output/light intensity may be converted to electrical signal using appropriate software (e.g., Genotyper™ and Sequence Navigator™, Perkin Elmer), and the entire process from loading of samples to computer analysis and electronic data display may be computer controlled. Capillary electrophoresis is especially preferable for sequencing small DNA fragments which may be present in limited amounts in a particular sample.

In another embodiment of the invention, polynucleotide sequences or fragments thereof which encode hChk1 may be cloned in recombinant DNA molecules that direct expression of hChk1, or fragments or functional equivalents thereof, in appropriate host cells. Due to the inherent degeneracy of the genetic code, other DNA sequences which encode substantially the same or a functionally equivalent amino acid sequence may be produced and used to express hChk1.

The nucleotide sequences of the present invention can be engineered using methods generally known in the art in order to alter hChk1-encoding sequences for a variety of purposes including, but not limited to, modification of the cloning, processing, and/or expression of the gene product. DNA shuffling by random fragmentation and PCR reassembly of gene fragments and synthetic oligonucleotides may be used to engineer the nucleotide sequences. For example, oligonucleotide-mediated site-directed mutagenesis may be used to introduce mutations that create new restriction sites, alter glycosylation patterns, change codon preference, produce splice variants, and so forth.

In another embodiment, sequences encoding hChk1 may be synthesized, in whole or in part, using chemical methods well known in the art. (See, e.g., Caruthers, M. H. et al. (1980) Nucl. Acids Res. Symp. Ser. 215–223, and Horn, T. et al. (1980) Nucl. Acids Res. Symp. Ser. 225–232.)

Alternatively, hChk1 itself or a fragment thereof may be synthesized using chemical methods. For example, peptide synthesis can be performed using various solid-phase techniques. (See, e.g., Roberge, J. Y. et al. (1995) Science 269:202–204.) Automated synthesis may be achieved using the ABI 431A Peptide Synthesizer (Perkin Elmer). Additionally, the amino acid sequence of hChk1, or any part thereof, may be altered during direct synthesis and/or combined with sequences from other proteins, or any part thereof, to produce a variant polypeptide.

The peptide may be substantially purified by preparative high performance liquid chromatography. (See, e.g, Chiez, R. M. and F. Z. Regnier (1990) Methods Enzymol. 182:392–421.) The composition of the synthetic peptides may be confirmed by amino acid analysis or by sequencing. (See, e.g., Creighton, T. (1984) *Proteins, Structures and Molecular Properties,* W H Freeman and Co., New York, N.Y.)

In order to express a biologically active hChk1, the nucleotide sequences encoding hChk1 or derivatives thereof may be inserted into an appropriate expression vector, i.e., a vector which contains the necessary elements for transcriptional and translational control of the inserted coding sequence in a suitable host. These elements include regulatory sequences, such as enhancers, constitutive and inducible promoters, and 5' and 3' untranslated regions in the vector and in polynucleotide sequences encoding hChk1. Such elements may vary in their strength and specificity. Specific initiation signals may also be used to achieve more efficient translation of sequences encoding hChk1. Such signals include the ATG initiation codon and adjacent sequences, e.g. the Kozak sequence. In cases where sequences encoding hChk1 and its initiation codon and upstream regulatory sequences are inserted into the appropriate expression vector, no additional transcriptional or translational control signals may be needed. However, in cases where only coding sequence, or a fragment thereof, is inserted, exogenous translational control signals including an in-frame ATG initiation codon should be provided by the vector. Exogenous translational elements and initiation codons may be of various origins, both natural and synthetic. The efficiency of expression may be enhanced by the inclusion of enhancers appropriate for the particular host cell system used. (See, e.g., Scharf, D. et al. (1994) Results Probl. Cell Differ. 20:125–162.)

Methods which are well known to those skilled in the art may be used to construct expression vectors containing sequences encoding hChk1 and appropriate transcriptional and translational control elements. These methods include in vitro recombinant DNA techniques, synthetic techniques, and in vivo genetic recombination. (See, e.g., Sambrook, J. et al. (1989) *Molecular Cloning, A Laboratory Manual,* Cold Spring Harbor Press, Plainview, N.Y., ch. 4, 8, and 16–17; and Ausubel, F. M. et al. (1995, and periodic supplements) *Current Protocols in Molecular Biology,* John Wiley & Sons, New York, N.Y., ch. 9, 13, and 16.)

A variety of expression vector/host systems may be utilized to contain and express sequences encoding hChk1. These include, but are not limited to, microorganisms such as bacteria transformed with recombinant bacteriophage, plasmid, or cosmid DNA expression vectors; yeast transformed with yeast expression vectors; insect cell systems infected with viral expression vectors (e.g., baculovirus); plant cell systems transformed with viral expression vectors (e.g., cauliflower mosaic virus (CaMV) or tobacco mosaic virus (TMV)) or with bacterial expression vectors (e.g., Ti or pBR322 plasmids); or animal cell systems. The invention is not limited by the host cell employed.

In bacterial systems, a number of cloning and expression vectors may be selected depending upon the use intended for polynucleotide sequences encoding hChk1. For example, routine cloning, subcloning, and propagation of polynucleotide sequences encoding hChk1 can be achieved using a multifunctional *E. coli* vector such as Bluescript® (Stratagene) or pSport1™ plasmid (GIBCO BRL). Ligation of sequences encoding hChk1 into the vector's multiple cloning site disrupts the lacZ gene, allowing a colorimetric screening procedure for identification of transformed bacteria containing recombinant molecules. In addition, these vectors may be useful for in vitro transcription, dideoxy sequencing, single strand rescue with helper phage, and creation of nested deletions in the cloned sequence. (See, e.g., Van Heeke, G. and S. M. Schuster (1989) J. Biol. Chem. 264:5503–5509.) When large quantities of hChk1 are needed, e.g. for the production of antibodies, vectors which direct high level expression of hChk1 may be used. For example, vectors containing the strong, inducible T5 or T7 bacteriophage promoter may be used.

Yeast expression systems may be used for production of hChk1. A number of vectors containing constitutive or inducible promoters, such as alpha factor, alcohol oxidase, and PGH, may be used in the yeast *Saccharomyces cerevisiae* or *Pichia pastoris*. In addition, such vectors direct either the secretion or intracellular retention of expressed proteins and enable integration of foreign sequences into the host genome for stable propagation. (See, e.g., Ausubel, supra; and Grant et al. (1987) Methods Enzymol. 153:516–54; Scorer, C. A. et al. (1994) Bio/Technology 12:181–184.)

Plant systems may also be used for expression of hChk1. Transcription of sequences encoding hChk1 may be driven viral promoters, e.g., the 35S and 19S promoters of CaMV used alone or in combination with the omega leader sequence from TMV. (Takamatsu, N. (1987) EMBO J. 6:307–311.) Alternatively, plant promoters such as the small subunit of RUBISCO or heat shock promoters may be used. (See, e.g., Coruzzi, G. et al. (1984) EMBO J. 3:1671–1680; Broglie, R. et al. (1984) Science 224:838–843; and Winter, J. et al. (1991) Results Probl. Cell Differ. 17:85–105.) These constructs can be introduced into plant cells by direct DNA transformation or pathogen-mediated transfection. (See, e.g., Hobbs, S. or Murry, L. E. in *McGraw Hill Yearbook of Science and Technology* (1992) McGraw Hill, New York, N.Y.; pp. 191–196.)

In mammalian cells, a number of viral-based expression systems may be utilized. In cases where an adenovirus is used as an expression vector, sequences encoding hChk1 may be ligated into an adenovirus transcription/translation complex consisting of the late promoter and tripartite leader sequence. Insertion in a non-essential E1 or E3 region of the viral genome may be used to obtain infective virus which expresses hChk1 in host cells. (See, e.g., Logan, J. and T. Shenk (1984) Proc. Natl. Acad. Sci. 81:3655–3659.) In addition, transcription enhancers, such as the Rous sarcoma virus (RSV) enhancer, may be used to increase expression in mammalian host cells. SV40 or EBV-based vectors may also be used for high-level protein expression.

Human artificial chromosomes (HACs) may also be employed to deliver larger fragments of DNA than can be contained in and expressed from a plasmid. HACs of about 6 kb to 10 Mb are constructed and delivered via conventional delivery methods (liposomes, polycationic amino polymers, or vesicles) for therapeutic purposes.

For long term production of recombinant proteins in mammalian systems, stable expression of hChk1 in cell lines is preferred. For example, sequences encoding hChk1 can be transformed into cell lines using expression vectors which may contain viral origins of replication and/or endogenous expression elements and a selectable marker gene on the same or on a separate vector. Following the introduction of the vector, cells may be allowed to grow for about 1 to 2 days in enriched media before being switched to selective media. The purpose of the selectable marker is to confer resistance to a selective agent, and its presence allows growth and recovery of cells which successfully express the introduced sequences. Resistant clones of stably transformed cells may be propagated using tissue culture techniques appropriate to the cell type.

Any number of selection systems may be used to recover transformed cell lines. These include, but are not limited to, the herpes simplex virus thymidine kinase and adenine phosphoribosyltransferase genes, for use in tk⁻ or apr⁻ cells, respectively. (See, e.g., Wigler, M. et al. (1977) Cell 11:223–232; and Lowy, I. et al. (1980) Cell 22:817–823.) Also, antimetabolite, antibiotic, or herbicide resistance can be used as the basis for selection. For example, dhfr confers resistance to methotrexate; neo confers resistance to the aminoglycosides neomycin and G-418; and als or pat confer resistance to chlorsulfuron and phosphinotricin acetyltransferase, respectively. (See, e.g., Wigler, M. et al. (1980) Proc. Natl. Acad. Sci. 77:3567–3570; Colbere-Garapin, F. et al (1981) J. Mol. Biol. 150:1–14; and Murry, supra.) Additional selectable genes have been described, e.g., trpB and hisD, which alter cellular requirements for metabolites. (See, e.g., Hartman, S. C. and R. C. Mulligan (1988) Proc. Natl. Acad. Sci. 85:8047–8051.) Visible markers, e.g., anthocyanins, green fluorescent proteins (GFP) (Clontech, Palo Alto, Calif.), β glucuronidase and its substrate β-D-glucuronoside, or luciferase and its substrate luciferin may be used. These markers can be used not only to identify transformants, but also to quantify the amount of transient or stable protein expression attributable to a specific vector system. (See, e.g., Rhodes, C. A. et al. (1995) Methods Mol. Biol. 55:121–131.)

Although the presence/absence of marker gene expression suggests that the gene of interest is also present, the presence and expression of the gene may need to be confirmed. For example, if the sequence encoding hChk1 is inserted within a marker gene sequence, transformed cells containing sequences encoding hChk1 can be identified by the absence of marker gene function. Alternatively, a marker gene can be placed in tandem with a sequence encoding hChk1 under the control of a single promoter. Expression of the marker gene in response to induction or selection usually indicates expression of the tandem gene as well.

In general, host cells that contain the nucleic acid sequence encoding hChk1 and that express hChk1 may be identified by a variety of procedures known to those of skill in the art. These procedures include, but are not limited to, DNA-DNA or DNA-RNA hybridizations, PCR amplification, and protein bioassay or immunoassay techniques which include membrane, solution, or chip based technologies for the detection and/or quantification of nucleic acid or protein sequences.

Immunological methods for detecting and measuring the expression of hChk1 using either specific polyclonal or monoclonal antibodies are known in the art. Examples of such techniques include enzyme-linked immunosorbent assays (ELISAs), radioimmunoassays (RIAs), and fluorescence activated cell sorting (FACS). A two-site, monoclonal-based immunoassay utilizing monoclonal antibodies reactive to two non-interfering epitopes on hChk1 is preferred, but a competitive binding assay may be employed. These and other assays are well known in the art. (See, e.g., Hampton, R. et al. (1990) Serological Methods, a Laboratory Manual, APS Press, St Paul, Minn., Section IV; Coligan, J. E. et al. (1997 and periodic supplements) Current Protocols in Immunology, Greene Pub. Associates and Wiley-Interscience, New York, N.Y.; and Maddox, D. E. et al. (1983) J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding hChk1 include oligolabeling, nick translation, end-labeling, or PCR amplification using a labeled nucleotide. Alternatively, the sequences encoding hChk1, or any fragments thereof, may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits, such as those provided by Pharmacia & Upjohn (Kalamazoo, Mich.), Promega (Madison, Wis.), and U.S. Biochemical Corp. (Cleveland, Ohio). Suitable reporter molecules or labels which may be used for ease of detection include radionuclides, enzymes, fluorescent, chemiluminescent, or chromogenic agents, as well as substrates, cofactors, inhibitors, magnetic particles, and the like.

Host cells transformed with nucleotide sequences encoding hChk1 may be cultured under conditions suitable for the expression and recovery of the protein from cell culture. The protein produced by a transformed cell may be secreted or retained intracellularly depending on the sequence and/or the vector used. As will be understood by those of skill in the art, expression vectors containing polynucleotides which encode hChk1 may be designed to contain signal sequences which direct secretion of hChk1 through a prokaryotic or eukaryotic cell membrane.

In addition, a host cell strain may be chosen for its ability to modulate expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to specify protein targeting, folding, and/or activity. Different host cells which have specific cellular machinery and characteristic mechanisms for post-translational activities (e.g., CHO, HeLa, MDCK, HEK293, and WI38), are available from the American Type Culture Collection (ATCC, Bethesda, Md.) and may be chosen to ensure the correct modification and processing of the foreign protein.

In another embodiment of the invention, natural, modified, or recombinant nucleic acid sequences encoding hChk1 may be ligated to a heterologous sequence resulting in translation of a fusion protein in any of the aforementioned host systems. For example, a chimeric hChk1 protein containing a heterologous moiety that can be recognized by a commercially available antibody may facilitate the screening of peptide libraries for inhibitors of hChk1 activity. Heterologous protein and peptide moieties may also facilitate purification of fusion proteins using commercially available affinity matrices. Such moieties include, but are not limited to, glutathione S-transferase (GST), maltose binding protein (MBP), thioredoxin (Trx), calmodulin binding peptide (CBP), 6-His, FLAG, c-myc, and hemagglutinin (HA). GST, MBP, Trx, CBP, and 6-His enable purification of their cognate fusion proteins on immobilized glutathione, maltose, phenylarsine oxide, calmodulin, and metal-chelate resins, respectively. FLAG, c-myc, and hemagglutinin (HA) enable immunoaffinity purification of fusion proteins using commercially available monoclonal and polyclonal antibodies that specifically recognize these epitope tags. A fusion protein may also be engineered to contain a proteolytic cleavage site located between the hChk1 encoding sequence and the heterologous protein sequence, so that hChk1 may be cleaved away from the heterologous moiety following purification. Methods for fusion protein expression and purification are discussed in Ausubel, F. M. et al. (1995 and periodic supplements) *Current Protocols in Molecular Biology*, John Wiley & Sons, New York, N.Y., ch 10. A variety of commercially available kits may also be used to facilitate expression and purification of fusion proteins.

In a further embodiment of the invention, synthesis of radiolabeled hChk1 may be achieved in vitro using the TNT™ rabbit reticulocyte lysate or wheat germ extract systems (Promega, Madison, Wis.). These systems couple transcription and translation of protein-coding sequences operably associated with the T7, T3, or SP6 promoters. Translation takes place in the presence of a radiolabeled amino acid precursor, preferably $^{35}$S-methionine.

Fragments of hChk1 may be produced not only by recombinant production, but also by direct peptide synthesis using solid-phase techniques. (See, e.g., Creighton, supra pp. 55–60.) Protein synthesis may be performed by manual techniques or by automation. Automated synthesis may be achieved, for example, using the Applied Biosystems 431A Peptide Synthesizer (Perkin Elmer). Various fragments of hChk1 may be synthesized separately and then combined to produce the full length molecule.

Therapeutics

Chemical and structural similarity, e.g., in the context of sequences and motifs, exists between hChk1 and checkpoint kinase from yeast (GI 311176). In addition, hChk1 is expressed in cancer and immortalized cell lines and in tissues associated with the immune response. Therefore, hChk1 appears to play a role in cancer and immune disorders.

Therefore, in one embodiment, hChk1 or a fragment or derivative thereof may be administered to a subject to treat or prevent a cancer. Such cancers can include, but are not limited to, adenocarcinoma, leukemia, lymphoma, melanoma, myeloma, sarcoma, and teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus.

In another embodiment, a vector capable of expressing hChk1 or a fragment or derivative thereof may be administered to a subject to treat or prevent a cancer including, but not limited to, those described above.

In a further embodiment, a pharmaceutical composition comprising a substantially purified hChk1 in conjunction with a suitable pharmaceutical carrier may be administered to a subject to treat or prevent a cancer including, but not limited to, those provided above.

In still another embodiment, an agonist which modulates the activity of hChk1 may be administered to a subject to treat or prevent a cancer including, but not limited to, those listed above.

In another embodiment, hChk1 or a fragment or derivative thereof may be administered to a subject to treat or prevent an immune disorder. Such disorders can include, but are not limited to, acquired immunodeficiency syndrome (AIDS), Addison's disease, adult respiratory distress syndrome, allergies, ankylosing spondylitis, amyloidosis, anemia, asthma, atherosclerosis, autoimmune hemolytic anemia, autoimmune thyroiditis, bronchitis, cholecystitis, contact dermatitis, Crohn's disease, atopic dermatitis, dermatomyositis, diabetes mellitus, emphysema, episodic lymphopenia with lymphocytotoxins, erythroblastosis fetalis, erythema nodosum, atrophic gastritis, glomerulonephritis, Goodpasture's syndrome, gout, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polymyositis, psoriasis, Reiter's syndrome, rheumatoid arthritis, scleroderma, Sjögren's syndrome, systemic anaphylaxis, systemic lupus erythematosus, systemic sclerosis, thrombocytopenic purpura, ulcerative colitis, uveitis, Werner syndrome, complications of cancer, hemodialysis, and extracorporeal circulation, viral, bacterial, fungal, parasitic, protozoal, and helminthic infections, and trauma.

In another embodiment, a vector capable of expressing hChk1 or a fragment or derivative thereof may be administered to a subject to treat or prevent an immune disorder including, but not limited to, those described above.

In a further embodiment, a pharmaceutical composition comprising a substantially purified hChk1 in conjunction with a suitable pharmaceutical carrier may be administered to a subject to treat or prevent an immune disorder including, but not limited to, those provided above.

In still another embodiment, an agonist which modulates the activity of hChk1 may be administered to a subject to treat or prevent an immune disorder including, but not limited to, those listed above.

In a further embodiment, an antagonist or inhibitor of hChk1 may be administered to a subject, either alone or in combination with radiation therapy or chemotherapy, to treat a cancer. Such a cancer may include, but is not limited to, those discussed above. In one aspect, an antibody which specifically binds hChk1 may be used directly as an antagonist or indirectly as a targeting or delivery mechanism for bringing a pharmaceutical agent to cells or tissue which express hChk1.

In an additional embodiment, a vector expressing a variant of hChk1 in which the ATP binding residue, K38, or the catalytic site residue, D130, are mutated to another amino acid to produce a dominantly acting, negative regulator of hChk1, may be administered to a subject, either alone or in combination with radiation therapy or chemotherapy, to treat a cancer including, but not limited to, those described above.

In other embodiments, any of the proteins, antagonists, antibodies, agonists, complementary sequences, or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of hChk1 may be produced using methods which are generally known in the art. In particular, purified hChk1 may be used to produce antibodies or to screen libraries of pharmaceutical agents to identify those which specifically bind hChk1. Antibodies to hChk1 may also be generated using methods that are well known in the art. Such antibodies may include, but are not limited to, polyclonal, monoclonal, chimeric, and single chain antibodies, Fab fragments, and fragments produced by a Fab expression library. Neutralizing antibodies (i.e., those which inhibit dimer formation) are especially preferred for therapeutic use.

For the production of antibodies, various hosts including goats, rabbits, rats, mice, humans, and others may be immunized by injection with hChk1 or with any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, KLH, and dinitrophenol. Among adjuvants used in humans, BCG (bacilli Calmette-Guerin) and *Corynebacterium parvum* are especially preferable.

It is preferred that the oligopeptides, peptides, or fragments used to induce antibodies to hChk1 have an amino acid sequence consisting of at least about 5 amino acids, and, more preferably, of at least about 10 amino acids. It is also preferable that these oligopeptides, peptides, or fragments are identical to a portion of the amino acid sequence of the natural protein and contain the entire amino acid sequence of a small, naturally occurring molecule. Short stretches of hChk1 amino acids may be fused with those of another protein, such as KLH, and antibodies to the chimeric molecule may be produced.

Monoclonal antibodies to hChk1 may be prepared using any technique which provides for the production of antibody molecules by continuous cell lines in culture. These include, but are not limited to, the hybridoma technique, the human B-cell hybridoma technique, and the EBV-hybridoma technique. (See, e.g., Kohler, G. et al. (1975) Nature 256:495–497; Kozbor, D. et al. (1985) J. Immunol. Methods 81:31–42; Cote, R. J. et al. (1983) Proc. Natl. Acad. Sci. 80:2026–2030; and Cole, S. P. et al. (1984) Mol. Cell Biol. 62:109–120.)

In addition, techniques developed for the production of "chimeric antibodies," such as the splicing of mouse antibody genes to human antibody genes to obtain a molecule with appropriate antigen specificity and biological activity, can be used. (See, e.g., Morrison, S. L. et al. (1984) Proc. Natl. Acad. Sci. 81:6851–6855; Neuberger, M. S. et al. (1984) Nature 312:604–608; and Takeda, S. et al. (1985) Nature 314:452–454.) Alternatively, techniques described for the production of single chain antibodies may be adapted, using methods known in the art, to produce hChk1-specific single chain antibodies. Antibodies with related specificity, but of distinct idiotypic composition, may be generated by chain shuffling from random combinatorial immunoglobulin libraries. (See, e.g., Burton D. R. (1991) Proc. Natl. Acad. Sci. 88:10134–10137.)

Antibodies may also be produced by inducing in vivo production in the lymphocyte population or by screening immunoglobulin libraries or panels of highly specific binding reagents as disclosed in the literature. (See, e.g., Orlandi, R. et al. (1989) Proc Natl. Acad. Sci. 86: 3833–3837; and Winter, G. et al. (1991) Nature 349:293–299.)

Antibody fragments which contain specific binding sites for hChk1 may also be generated. For example, such fragments include, but are not limited to, F(ab')2 fragments produced by pepsin digestion of the antibody molecule and Fab fragments generated by reducing the disulfide bridges of the F(ab')2 fragments. Alternatively, Fab expression libraries may be constructed to allow rapid and easy identification of monoclonal Fab fragments with the desired specificity. (See, e.g., Huse, W. D. et al. (1989) Science 246:1275–1281.)

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between hChk1 and its specific antibody. A two-site, monoclonal-based immunoassay utilizing monoclonal antibodies reactive to two non-interfering hChk1 epitopes is preferred, but a competitive binding assay may also be employed. (Maddox, supra.)

In another embodiment of the invention, the polynucleotides encoding hChk1, or any fragment or complement thereof, may be used for therapeutic purposes. In one aspect, the complement of the polynucleotide encoding hChk1 may be used in situations in which it would be desirable to block the transcription of the mRNA. In particular, cells may be transformed with sequences complementary to polynucleotides encoding hChk1. Thus, complementary molecules or fragments may be used to modulate hChk1 activity, or to achieve regulation of gene function. Such technology is now well known in the art, and sense or antisense oligonucleotides or larger fragments can be designed from various locations along the coding or control regions of sequences encoding hChk1.

Expression vectors derived from retroviruses, adenoviruses, or herpes or vaccinia viruses, or from various bacterial plasmids, may be used for delivery of nucleotide sequences to the targeted organ, tissue, or cell population. Methods which are well known to those skilled in the art can be used to construct vectors to express nucleic acid sequences complementary to the polynucleotides encoding hChk1. (See, e.g., Sambrook, supra; and Ausubel, supra.)

Genes encoding hChk1 can be turned off by transforming a cell or tissue with expression vectors which express high levels of a polynucleotide, or fragment thereof, encoding hChk1. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector, and may last even longer if appropriate replication elements are part of the vector system.

As mentioned above, modifications of gene expression can be obtained by designing complementary sequences or antisense molecules (DNA, RNA, or PNA) to the control, 5', or regulatory regions of the gene encoding hChk1. Oligonucleotides derived from the transcription initiation site, e.g., between about positions −10 and +10 from the start site, are preferred. Similarly, inhibition can be achieved using triple helix base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature. (See, e.g., Gee, J. E. et al. (1994) in Huber, B. E. and B. I. Carr, *Molecular and Immunologic Approaches,* Futura Publishing Co., Mt. Kisco, N.Y., pp. 163–177.) A complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. For example, engineered hammerhead motif ribozyme molecules may specifically and efficiently catalyze endonucleolytic cleavage of sequences encoding hChk1.

Specific ribozyme cleavage sites within any potential RNA target are initially identified by scanning the target molecule for ribozyme cleavage sites, including the following sequences: GUA, GUU, and GUC. Once identified, short RNA sequences of between 15 and 20 ribonucleotides, corresponding to the region of the target gene containing the cleavage site, may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding hChk1. Such DNA sequences may be incorporated into a wide variety of vectors with suitable RNA polymerase promoters such as T7 or SP6. Alternatively, these cDNA constructs that synthesize complementary RNA, constitutively or inducibly, can be introduced into cell lines, cells, or tissues.

RNA molecules may be modified to increase intracellular stability and half-life. Possible modifications include, but are not limited to, the addition of flanking sequences at the 5' and/or 3' ends of the molecule, or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections, or by polycationic amino polymers may be achieved using methods which are well known in the art. (See, e.g., Goldman, C. K. et al. (1997) Nature Biotechnology 15:462–466.)

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical or sterile composition, in conjunction with a pharmaceutically acceptable carrier, for any of the therapeutic effects discussed above. Such pharmaceutical compositions may consist of hChk1, antibodies to hChk1, and mimetics, agonists, antagonists, or inhibitors of hChk1. The compositions may be administered alone or in combination with at least one other agent, such as a stabilizing compound, which may be administered in any sterile, biocompatible pharmaceutical carrier including, but not limited to, saline, buffered saline, dextrose, and water. The compositions may be administered to a patient alone, or in combination with other agents, drugs, or hormones.

The pharmaceutical compositions utilized in this invention may be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combining active compounds with solid excipient and processing the resultant mixture of granules (optionally, after grinding) to obtain tablets or dragee cores. Suitable auxiliaries can be added, if desired. Suitable excipients include carbohydrate or protein fillers, such as sugars, including lactose, sucrose, mannitol, and sorbitol; starch from corn, wheat, rice, potato, or other plants; cellulose, such as methyl cellulose, hydroxypropylmethyl-cellulose, or sodium carboxymethylcellulose; gums, including arabic and tragacanth; and proteins, such as gelatin and collagen. If desired, disintegrating or solubilizing agents may be added, such as the cross-linked polyvinyl pyrrolidone, agar, and alginic acid or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with fillers or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also contain suitable stabilizers or agents to increase the solubility of the compounds and allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, and succinic acid. Salts tend to be more soluble in aqueous or other protonic solvents than are the corresponding free base forms. In other cases, the preferred preparation may be a lyophilized powder which may contain any or all of the following: 1 mM to 50 mM histidine, 0.1% to 2% sucrose, and 2% to 7% mannitol, at a pH range of 4.5 to 5.5, that is combined with buffer prior to use.

After pharmaceutical compositions have been prepared, they can be placed in an appropriate container and labeled for treatment of an indicated condition. For administration of hChk1, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells or in animal models such as mice, rats, rabbits, dogs, or pigs. An animal model may also be used to determine the appropriate concentration range and route of administration. Such information can then be used to determine useful doses and routes for administration in humans.

A therapeutically effective dose refers to that amount of active ingredient, for example hChk1 or fragments thereof, antibodies of hChk1, and agonists, antagonists or inhibitors of hChk1, which ameliorates the symptoms or condition. Therapeutic efficacy and toxicity may be determined by standard pharmaceutical procedures in cell cultures or with experimental animals, such as by calculating the $ED_{50}$ (the dose therapeutically effective in 50% of the population) or $LD_{50}$ (the dose lethal to 50% of the population) statistics. The dose ratio of toxic to therapeutic effects is the therapeutic index, and it can be expressed as the $LD_{50}/ED_{50}$ ratio. Pharmaceutical compositions which exhibit large therapeutic indices are preferred. The data obtained from cell culture assays and animal studies are used to formulate a range of dosage for human use. The dosage contained in such compositions is preferably within a range of circulating concentrations that includes the $ED_{50}$ with little or no toxicity. The dosage varies within this range depending upon the dosage form employed, the sensitivity of the patient, and the route of administration.

The exact dosage will be determined by the practitioner, in light of factors related to the subject requiring treatment. Dosage and administration are adjusted to provide sufficient levels of the active moiety or to maintain the desired effect. Factors which may be taken into account include the severity of the disease state, the general health of the subject, the age, weight, and gender of the subject, time and frequency of administration, drug combination(s), reaction sensitivities, and response to therapy. Long-acting pharmaceutical compositions may be administered every 3 to 4 days, every week, or biweekly depending on the half-life and clearance rate of the particular formulation.

Normal dosage amounts may vary from about 0.1 $\mu$g to 100,000 $\mu$g, up to a total dose of about 1 gram, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

Diagnostics

In another embodiment, antibodies which specifically bind hChk1 may be used for the diagnosis of disorders characterized by expression of hChk1, or in assays to monitor patients being treated with hChk1 or agonists, antagonists, or inhibitors of hChk1. Antibodies useful for diagnostic purposes may be prepared in the same manner as described above for therapeutics. Diagnostic assays for hChk1 include methods which utilize the antibody and a label to detect hChk1 in human body fluids or in extracts of cells or tissues. The antibodies may be used with or without modification, and may be labeled by covalent or non-covalent attachment of a reporter molecule. A wide variety of reporter molecules, several of which are described above, are known in the art and may be used.

A variety of protocols for measuring hChk1, including ELISAs, RIAs, and FACS, are known in the art and provide a basis for diagnosing altered or abnormal levels of hChk1 expression. Normal or standard values for hChk1 expression are established by combining body fluids or cell extracts taken from normal mammalian subjects, preferably human, with antibody to hChk1 under conditions suitable for complex formation. The amount of standard complex formation may be quantitated by various methods, preferably by photometric means. Quantities of hChk1 expressed in samples, control, and disease, from biopsied tissues are compared with the standard values. Deviation between standard and subject values establishes the parameters for diagnosing disease.

In another embodiment of the invention, the polynucleotides encoding hChk1 may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of hChk1 may be correlated with disease. The diagnostic assay may be used to determine absence, presence, and excess expression of hChk1, and to monitor regulation of hChk1 levels during therapeutic intervention.

In one aspect, hybridization with PCR probes which are capable of detecting polynucleotide sequences, including genomic sequences, encoding hChk1 or closely related molecules may be used to identify nucleic acid sequences which encode hChk1. The specificity of the probe, whether it is made from a highly specific region, e.g., the 5' regulatory region, or from a less specific region, e.g., a conserved motif, and the stringency of the hybridization or amplification (maximal, high, intermediate, or low), will determine whether the probe identifies only naturally occurring sequences encoding hChk1, allelic variants, or related sequences.

Probes may also be used for the detection of related sequences, and should preferably have at least 50% sequence identity to any of the hChk1 encoding sequences. The hybridization probes of the subject invention may be DNA or RNA and may be derived from the sequence of SEQ ID NO:2 or from genomic sequences including promoters, enhancers, and introns of the hChk1 gene.

Means for producing specific hybridization probes for DNAs encoding hChk1 include the cloning of polynucleotide sequences encoding hChk1 or hChk1 derivatives into vectors for the production of mRNA probes. Such vectors are known in the art, are commercially available, and may be used to synthesize RNA probes in vitro by means of the addition of the appropriate RNA polymerases and the appropriate labeled nucleotides. Hybridization probes may be labeled by a variety of reporter groups, for example, by radionuclides such as $^{32}P$ or $^{35}S$, or by enzymatic labels, such as alkaline phosphatase coupled to the probe via avidin/biotin coupling systems, and the like.

Polynucleotide sequences encoding hChk1 may be used for the diagnosis of a disorder associated with expression of hChk1. Examples of such a disorder include, but are not limited to, cancers, such as adenocarcinoma, leukemia, lymphoma, melanoma, myeloma, sarcoma, and teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus, and immune disorders such as acquired immunodeficiency syndrome (AIDS), Addison's disease, adult respiratory distress syndrome, allergies, ankylosing spondylitis, amyloidosis, anemia, asthma, atherosclerosis, autoimmune hemolytic anemia, autoimmune thyroiditis, bronchitis, cholecystitis, contact dermatitis, Crohn's disease, atopic dermatitis, dermatomyositis, diabetes mellitus, emphysema, episodic lymphopenia with lymphocytotoxins, erythroblastosis fetalis, erythema nodosum, atrophic gastritis, glomerulonephritis, Goodpasture's syndrome, gout, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polymyositis, psoriasis, Reiter's syndrome, rheumatoid arthritis, scleroderma, Sjögren's syndrome, systemic anaphylaxis, systemic lupus erythematosus, systemic sclerosis, thrombocytopenic purpura, ulcerative colitis, uveitis, Werner syndrome, complications of cancer, hemodialysis, and extracorporeal circulation, viral, bacterial, fungal, parasitic, protozoal, and helminthic infections, and trauma. The polynucleotide sequences encoding hChk1 may be used in Southern or northern analysis, dot blot, or other membrane-based technologies; in PCR technologies; in dipstick, pin, and ELISA assays; and in microarrays utilizing fluids or tissues from patients to detect altered hChk1 expression. Such qualitative or quantitative methods are well known in the art.

In a particular aspect, the nucleotide sequences encoding hChk1 may be useful in assays that detect the presence of associated disorders, particularly those mentioned above. The nucleotide sequences encoding hChk1 may be labeled by standard methods and added to a fluid or tissue sample from a patient under conditions suitable for the formation of hybridization complexes. After a suitable incubation period, the sample is washed and the signal is quantitated and compared with a standard value. If the amount of signal in the patient sample is significantly altered in comparison to a control sample then the presence of altered levels of nucleotide sequences encoding hChk1 in the sample indicates the presence of the associated disorder. Such assays may also be used to evaluate the efficacy of a particular therapeutic treatment regimen in animal studies, in clinical trials, or to monitor the treatment of an individual patient.

In order to provide a basis for the diagnosis of a disorder associated with expression of hChk1, a normal or standard profile for expression is established. This may be accomplished by combining body fluids or cell extracts taken from normal subjects, either animal or human, with a sequence, or a fragment thereof, encoding hChk1, under conditions suitable for hybridization or amplification. Standard hybridization may be quantified by comparing the values obtained from normal subjects with values from an experiment in which a known amount of a substantially purified polynucleotide is used. Standard values obtained in this manner may be compared with values obtained from samples from patients who are symptomatic for a disorder. Deviation from standard values is used to establish the presence of a disorder.

Once the presence of a disorder is established and a treatment protocol is initiated, hybridization assays may be repeated on a regular basis to determine if the level of expression in the patient begins to approximate that which is observed in the normal subject. The results obtained from successive assays may be used to show the efficacy of treatment over a period ranging from several days to months.

With respect to cancer, the presence of a relatively high amount of transcript, or an abnormally low amount, in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding hChk1 may involve the use of PCR. These oligomers may be chemically synthesized, generated enzymatically, or produced in vitro. Oligomers will preferably contain a fragment of a polynucleotide encoding hChk1, or a fragment of a polynucleotide complementary to the polynucleotide encoding hChk1, and will be employed under optimized conditions for identification of a specific gene or condition. Oligomers may also be employed under less stringent conditions for detection or quantitation of closely related DNA or RNA sequences.

Methods which may also be used to quantitate the expression of hChk1 include radiolabeling or biotinylating nucleotides, coamplification of a control nucleic acid, and interpolating results from standard curves. (See, e.g., Melby, P. C. et al. (1993) J. Immunol. Methods 159:235–244; and Duplaa, C. et al. (1993) Anal. Biochem. 229–236.) The speed of quantitation of multiple samples may be accelerated by running the assay in an ELISA format where the oligomer of interest is presented in various dilutions and a spectrophotometric or colorimetric response gives rapid quantitation.

In further embodiments, oligonucleotides or longer fragments derived from any of the polynucleotide sequences described herein may be used as targets in a microarray. The microarray can be used to monitor the expression level of large numbers of genes simultaneously and to identify genetic variants, mutations, and polymorphisms. This information may be used to determine gene function, to understand the genetic basis of a disorder, to diagnose a disorder, and to develop and monitor the activities of therapeutic agents.

Microarrays may be prepared, used, and analyzed using methods known in the art. (See, e.g., Brennan, T. M. et al. (1995) U.S. Pat. No. 5,474,796; Schena, M. et al. (1996) Proc. Natl. Acad. Sci. 93:10614–10619; Baldeschweiler et al. (1995) PCT application WO95/251116; Shalon, D. et al. (1995) PCT application WO95/35505; Heller, R. A. et al. (1997) Proc. Natl. Acad. Sci. 94:2150–2155; and Heller, M. J. et al. (1997) U.S. Pat. No. 5,605,662.)

In another embodiment of the invention, nucleic acid sequences encoding hChk1 may be used to generate hybridization probes useful in mapping the naturally occurring genomic sequence. The sequences may be mapped to a particular chromosome, to a specific region of a chromosome, or to artificial chromosome constructions, e.g., human artificial chromosomes (HACs), yeast artificial chromosomes (YACs), bacterial artificial chromosomes (BACs), bacterial P1 constructions, or single chromosome cDNA libraries. (See, e.g., Price, C. M. (1993) Blood Rev. 7:127–134; and Trask, B. J. (1991) Trends Genet. 7:149–154.)

Fluorescent in situ hybridization (FISH) may be correlated with other physical chromosome mapping techniques and genetic map data. (See, e.g., Heinz-Ulrich, et al. (1995) in Meyers, R. A. (ed.) *Molecular Biology and Biotechnology*, VCH Publishers New York, N.Y., pp. 965–968.) Examples of genetic map data can be found in various scientific journals or at the Online Mendelian Inheritance in Man (OMIM) site. Correlation between the location of the gene encoding hChk1 on a physical chromosomal map and a specific disorder, or a predisposition to a specific disorder, may help define the region of DNA associated with that disorder. The nucleotide sequences of the invention may be used to detect differences in gene sequences among normal, carrier, and affected individuals.

In situ hybridization of chromosomal preparations and physical mapping techniques, such as linkage analysis using established chromosomal markers, may be used for extending genetic maps. Often the placement of a gene on the chromosome of another mammalian species, such as mouse, may reveal associated markers even if the number or arm of a particular human chromosome is not known. New sequences can be assigned to chromosomal arms by physical mapping. This provides valuable information to investigators searching for disease genes using positional cloning or other gene discovery techniques. Once the disease or syndrome has been crudely localized by genetic linkage to a particular genomic region, e.g., ataxia-telangiectasia to 11q22-23, any sequences mapping to that area may represent associated or regulatory genes for further investigation. (See, e.g., Gatti, R. A. et al. (1988) Nature 336:577–580.) The nucleotide sequence of the subject invention may also be used to detect differences in the chromosomal location due to translocation, inversion, etc., among normal, carrier, or affected individuals.

In another embodiment of the invention, hChk1, its catalytic or immunogenic fragments, or oligopeptides thereof can be used for screening libraries of compounds in any of a variety of drug screening techniques. The fragment employed in such screening may be free in solution, affixed to a solid support, borne on a cell surface, or located intracellularly. The formation of binding complexes between hChk1 and the agent being tested may be measured.

Another technique for drug screening provides for high throughput screening of compounds having suitable binding affinity to the protein of interest. (See, e.g., Geysen, et al. (1984) PCT application WO84/03564.) In this method, large numbers of different small test compounds are synthesized on a solid substrate, such as plastic pins or some other surface. The test compounds are reacted with hChk1, or fragments thereof, and washed. Bound hChk1 is then detected by methods well known in the art. Purified hChk1 can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding hChk1 specifically compete with a test compound for binding hChk1. In this manner, antibodies can be used to detect the presence of any peptide which shares one or more antigenic determinants with hChk1.

In additional embodiments, the nucleotide sequences which encode hChk1 may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I. MMLR1DT01 cDNA Library Construction

The normal peripheral blood macrophages used for this library were obtained from two 24 year old, Caucasian males. The MMLR1DT01 library represents a mixture of allogeneically stimulated human macrophage populations obtained from Ficoll/Hypaque purified buffy coats. The cells from the two different donors (not typed for HLA alleles) were incubated at a density of 1×10$^6$/ml for 48 hours in DME containing 10% human serum.

After incubation, macrophages mostly adhered to the plastic surface of the petri dish, and most other cell types, B and T lymphocytes, remained in solution. The DME was decanted from the wells, and the wells were washed with phosphate buffered saline (PBS). Macrophages were released from the plastic surface by gently scraping the petri dishes in PBS/1 mM EDTA. Macrophages were lysed immediately in buffer containing guanidinium isothiocyanate.

The lysate was extracted twice with a mixture of acid phenol pH 4.0 and centrifuged over a CsCl cushion using a Beckman SW28 rotor in a L8-70M Ultracentrifuge (Beckman Instruments). The RNA was precipitated using 0.3 M sodium acetate and 2.5 volumes of ethanol, resuspended in water and treated with DNase for 15 min at 37° C. It must be noted that some contaminating T and B lymphocytes may have been present.

The RNA was used in the SuperScript Plasmid System for cDNA synthesis and plasmid cloning (Life Technologies, Gaithersburg Md.) with the recommended protocol. cDNAs were fractionated on a Sepharose CL4B column (catalog #275105, Pharmacia Biotech, Pistcataway, N.J.) and those cDNAs exceeding 400 bp were ligated into pSport I. The plasmid was transformed into chemically competent DH5α host cells (Life Technologies).

II. Isolation and Sequencing of cDNA Clones

Plasmid DNA was released from the cells and purified using the Miniprep Kit (Advanced Genetic Technologies Corporation, Gaithersburg Md.). The recommended protocol was employed except for the following changes: 1) the 96 wells were each filled with only 1 ml of sterile Terrific Broth (Life Technologies) with carbenicillin at 25 mg/L and glycerol at 0.4%; 2) the bacteria were cultured for 24 hours after the wells were inoculated and then lysed with 60 µl of lysis buffer; 3) a centrifugation step employing the Beckman GS-6R @ 2900 rpm for 5 min was performed before the contents of the block were added to the primary filter plate; and 4) the optional step of adding isopropanol to TRIS buffer was not routinely performed. After the last step in the protocol, samples were transferred to a Beckman 96-well block for storage.

The cDNAs were prepared using a Hamilton Micro Lab 2200 (Hamilton, Reno Nev.) in combination with four Peltier Thermal Cyclers (PTC200 from MJ Research, Watertown Mass.). The cDNAs were sequenced by the method of Sanger F and AR Coulson (1975; J Mol Biol 94:441f) using ABI 377 or 373 DNA Sequencing Systems (Perkin Elmer), and reading frame was determined.

III. Analysis of cDNA Clones and their Deduced Proteins

The cDNA sequences and the full length nucleotide and amino acid sequences disclosed in the Sequence Listing were queried against databases such as GenBank primate (pri), rodent (rod), mammalian (mamp), vertebrate (vrtp), and eukaryote (eukp) databases, SwissProt, BLOCKS, and other databases which contain previously identified and annotated motifs and sequences. Algorithms such as Smith Waterman which deal with primary sequence patterns and secondary structure gap penalties (Smith, T. et al. (1992) Protein Engineering 5:35–51) and programs and algorithms such as BLAST (Basic Local Alignment Search Tool; Altschul, S. F. (1993) J. Mol. Evol 36:290–300; and Altschul et al. (1990) J. Mol. Biol. 215:403–410), and HMM (Hidden Markov Models; Eddy, S. R. (1996) Cur. Opin. Str. Biol. 6:361–365 and Sonnhammer, E. L. L. et al. (1997) Proteins 28:405–420) were used to assemble and analyze nucleotide and amino acid sequences. The databases, programs, algorithms, methods and tools are available, well known in the art, and described in Ausubel (supra, unit 7.7), in Meyers, R. A. (1995; *Molecular Biology and Biotechnology*, Wiley VCH, Inc, New York N.Y., p 856–853), in documentation provided with software (Genetics Computer Group (GCG), Madison Wis.), and on the world wide web (www). Two comprehensive websites which list, describe, and/or link many of the databases and tools are: 1) the www resource in practical sequence analysis (http://genome.wustl.edu/eddy/bio5495/online_resources.html), and 2) the bibliography of computational gene recognition (http://linkage.rockefeller.edu/wli/gene/programs.html). For example, the first website links PFAM as a database (http://genome.wustl.edu/Pfam/) and as an HMM search tool (http://genome.wustl.edu/eddy/cgi-bin/hmm_page.cgi).

Table 1 summarizes the databases and tools used herein. The first column of Table 1 shows the tool, program, or algorithm; the second column, the database; the third column, a brief description; and the fourth column (where applicable), scores for determining the strength of a match between two sequences (the higher the value, the more homologous).

IV. Northern Analysis

Northern analysis is a laboratory technique used to detect the presence of a transcript of a gene and involves the hybridization of a labeled nucleotide sequence to a membrane on which RNAs from a particular cell type or tissue have been bound. (See, e.g., Sambrook, supra, ch. 7; and Ausubel, supra, ch. 4 and 16.)

Analogous computer techniques applying BLAST were used to search for identical or related molecules in databases such as GenBank or LIFESEQ™ database (Incyte Pharmaceuticals). This analysis is much faster than multiple membrane-based hybridizations. In addition, the sensitivity of the computer search can be modified to determine whether any particular match is categorized as exact or similar.

The basis of the search is the product score, which is defined as:

$$\% \text{ sequence identity} \times \% \text{ maximum BLAST score}/100$$

The product score takes into account both the degree of similarity between two sequences and the length of the sequence match. For example, with a product score of 40, the match will be exact within a 1% to 2% error, and, with a product score of 70, the match will be exact. Similar molecules are usually identified by selecting those which show product scores between 15 and 40, although lower scores may identify related molecules.

The results of Northern analysis are shown in FIG. 4, giving the list of libraries in which the transcript encoding hChk1 was found. Abundance and percent abundance are also reported. Abundance directly reflects the number of times a particular transcript is represented in a cDNA library, and percent abundance is abundance divided by the total number of sequences examined in the cDNA library.

V. Extension of hChk1 Encoding Polynucleotides

Oligonucleotide primers were designed from clones 516219 and 2044650 for PCR to enable full length construction of hChk1. Oligonucleotide 1 (5' GTGAATTCA-CCACCATGGCAGTGCCCTTTGTGGAAGACTGGGA-CTTGGTGCAAACCCTGGGAGAAGGTGCCTATGGA-GAAGTTCAAC 3'; SEQ ID NO:13) was extended by PCR to complete the 5' end of cDNA clone 2044650 inclusive of the ATG start codon (in the context of a kozak consensus sequence) and an EcoR1 restriction site. Oligonucleotide 2 (5' CACTCGAGGATTCCCCAGAGCCGATGGTC 3'; SEQ ID NO:14) was extended by PCR to complete the 3' end of cDNA clone 516219 inclusive of the TGA stop codon and an Xho1 restriction site. Oligonucleotide 3 (5' GGAATAACTCACAGGGATATTAAACCA-GAAAATCTTCTGTTGGATGAAAGGGATAAC 3'; SEQ ID NO:15), derived from the consensus sequence, was used to bridge the gap between clones 516219 and 2044650.

VI. Labeling and Use of Individual Hybridization Probes

Hybridization probes derived from SEQ ID NO:2 are employed to screen cDNAs, genomic DNAs, or mRNAs. Although the labeling of oligonucleotides, consisting of about 20 base pairs, is specifically described, essentially the same procedure is used with larger nucleotide fragments. Oligonucleotides are designed using state-of-the-art software such as OLIGO™ 4.06 software (National Biosciences) and labeled by combining 50 pmol of each oligomer, 250 $\mu$Ci of [$\gamma$-$^{32}$P] adenosine triphosphate (Amersham, Chicago, Ill.), and T4 polynucleotide kinase (DuPont NEN®, Boston, Mass.). The labeled oligonucleotides are substantially purified using a Sephadex™ G-25 superfine size exclusion dextran bead column (Pharmacia & Upjohn, Kalamazoo, Mich.). An aliquot containing $10^7$ counts per minute of the labeled probe is used in a typical membrane-based hybridization analysis of human genomic DNA digested with one of the following endonucleases: Ase I, Bgl II, Eco RI, Pst I, Xba1, or Pvu II (DuPont NEN, Boston, Mass.).

The DNA from each digest is fractionated on a 0.7% agarose gel and transferred to nylon membranes (Nytran Plus, Schleicher & Schuell, Durham, N.H.). Hybridization is carried out for 16 hours at 40° C. To remove nonspecific signals, blots are sequentially washed at room temperature under increasingly stringent conditions up to 0.1×saline sodium citrate and 0.5% sodium dodecyl sulfate. After XOMAT AR film (Kodak, Rochester, N.Y.) is exposed to the blots to film for several hours, hybridization patterns are compared visually.

VII. Microarrays

A chemical coupling procedure and an ink jet device can be used to synthesize array elements on the surface of a substrate. (See, e.g., Baldeschweiler, supra.) An array analogous to a dot or slot blot may also be used to arrange and link elements to the surface of a substrate using thermal, UV, chemical, or mechanical bonding procedures. A typical array may be produced by hand or using available methods and machines and contain any appropriate number of elements. After hybridization, nonhybridized probes are removed and a scanner used to determine the levels and patterns of fluorescence. The degree of complementarity and the relative abundance of each probe which hybridizes to an element on the microarray may be assessed through analysis of the scanned images.

Full-length cDNAs, Expressed Sequence Tags (ESTs), or fragments thereof may comprise the elements of the microarray. Fragments suitable for hybridization can be selected using software well known in the art such as LASERGENE™. Full-length cDNAs, ESTs, or fragments thereof corresponding to one of the nucleotide sequences of the present invention, or selected at random from a cDNA library relevant to the present invention, are arranged on an appropriate substrate, e.g., a glass slide. The cDNA is fixed to the slide using, e.g., UV cross-linking followed by thermal and chemical treatments and subsequent drying. (See, e.g., Schena, M. et al. (1995) Science 270:467–470; and Shalon, D. et al. (1996) Genome Res. 6:639–645.) Fluorescent probes are prepared and used for hybridization to the elements on the substrate. The substrate is analyzed by procedures described above.

VIII. Complementary Polynucleotides

Sequences complementary to the hChk1 -encoding sequences, or any parts thereof, are used to detect, decrease, or inhibit expression of naturally occurring hChk1. Although use of oligonucleotides comprising from about 15 to 30 base pairs is described, essentially the same procedure is used with smaller or with larger sequence fragments. Appropriate oligonucleotides are designed using OLIGO™ 4.06 software and the coding sequence of hChk1. To inhibit transcription, a complementary oligonucleotide is designed from the most unique 5' sequence and used to prevent promoter binding to the coding sequence. To inhibit translation, a complementary oligonucleotide is designed to prevent ribosomal binding to the hChk1 -encoding transcript.

IX. Expression of hChk1

Expression and purification of hChk1 was achieved using various bacterial, mammalian, or virus-based expression systems. Vectors were constructed using both active hChk1 kinase (SEQ ID NO:2) and an inactive kinase (K38A; SEQ ID NO:16) achieved by changing amino acid K38 in SEQ ID NO:1 to alanine (A38) by nucleotide base changes in SEQ ID NO:2 from A128 AG to G128CG. Table 2 summarizes the various expression vectors, host cells, and their sources used in the expression of these sequences.

TABLE 2

| Vector | Host Cell | Source |
| --- | --- | --- |
| pGex4T3 | E. coli | Pharmacia Biotech |
| pFastBac | Insect | Life Technologies |
| pFastBac HTC | Insect | Life Technologies |
| pIND | Mammalian | Invitrogen, Carlsbad, CA |
| pcDNA3.1 | Mammalian | Invitrogen | hChk1 obtained by these methods were used directly in the following activity assay.

X. Demonstration of hChk1 Activity

Protein kinase activity of hChk1 was demonstrated in vitro in an assay containing hChk1, 50 $\mu$l of kinase buffer, 1 $\mu$g substrate, such as mylein basic protein (MBP) or synthetic peptide substrates, 1 mM DTT, 10 $\mu$g ATP, and 0.5 $\mu$Ci [$\gamma$-$^{33}$P]ATP. The reaction was incubated at 30° C. for 30 minutes and stopped by pipetting onto P81 paper. The incorporated radioactivity was measured using a radioactivity scintillation counter. Alternatively, the reaction was stopped by heating to 100° C. in the presence of SDS loading buffer and visualized on a 12% SDS polyacrylamide gel by autoradiography. Incorporated radioactivity was corrected for reactions carried out in the absence of hChk1 or in the presence of the inactive kinase, K38A (SEQ ID NO:16).

In the alternative, other assays for hChk1 might include scintillation proximity assays (SPA), scintillation plate technology and filter binding assays. Useful substrates include recombinant proteins tagged with glutathione transferase, or synthetic peptide substrates tagged with biotin. Inhibitors of hChk1 activity, such as small organic molecules, proteins or peptides, may be identified by such assays.

XI. Functional Assays hChk1 function is assessed by expressing the sequences encoding hChk1 at physiologically elevated levels in mammalian cell culture systems. cDNA is subcloned into a mammalian expression vector containing a strong promoter that drives high levels of cDNA expression. Vectors of choice include pCMV SPORT™ (Life Technologies, Gaithersburg, Md.) and pCR™ 3.1 (Invitrogen, Carlsbad, Calif., both of which contain the cytomegalovirus promoter. 5–10 µg of recombinant vector are transiently transfected into a human cell line, preferably of endothelial or hematopoietic origin, using either liposome formulations or electroporation. 1–2 µg of an additional plasmid containing sequences encoding a marker protein are co-transfected. Expression of a marker protein provides a means to distinguish transfected cells from nontransfected cells and is a reliable predictor of cDNA expression from the recombinant vector. Marker proteins of choice include, e.g., Green Fluorescent Protein (GFP) (Clontech, Palo Alto, Calif.), CD64, or a CD64-GFP fusion protein. Flow cytometry (FCM), an automated, laser optics-based technique, is used to identify transfected cells expressing GFP or CD64-GFP, and to evaluate properties, for example, their apoptotic state. FCM detects and quantifies the uptake of fluorescent molecules that diagnose events preceding or coincident with cell death. These events include changes in nuclear DNA content as measured by staining of DNA with propidium iodide; changes in cell size and granularity as measured by forward light scatter and 90 degree side light scatter; downregulation of DNA synthesis as measured by decrease in bromodeoxyuridine uptake; alterations in expression of cell surface and intracellular proteins as measured by reactivity with specific antibodies; and alterations in plasma membrane composition as measured by the binding of fluorescein-conjugated Annexin V protein to the cell surface. Methods in flow cytometry are discussed in Ormerod, M. G. (1994) *Flow Cytometry*, Oxford, New York, N.Y.

The influence of hChk1 on gene expression can be assessed using highly purified populations of cells transfected with sequences encoding hChk1 and either CD64 or CD64-GFP. CD64 and CD64-GFP are expressed on the surface of transfected cells and bind to conserved regions of human immunoglobulin G (IgG). Transfected cells are efficiently separated from nontransfected cells using magnetic beads coated with either human IgG or antibody against CD64 (DYNAL, Lake Success, N.Y.). mRNA can be purified from the cells using methods well known by those of skill in the art. Expression of mRNA encoding hChk1 and other genes of interest can be analyzed by Northern analysis or microarray techniques.

XII. Production of hChk1 Specific Antibodies hChk1 substantially purified using polyacrylamide gel electrophoresis (PAGE)(see, e.g., Harrington, M. G. (1990) Methods Enzymol. 182:488–495), or other purification techniques, is used to immunize rabbits and to produce antibodies using standard protocols.

Alternatively, the hChk1 amino acid sequence is analyzed using LASERGENE™ software (DNASTAR Inc.) to determine regions of high immunogenicity, and a corresponding oligopeptide is synthesized and used to raise antibodies by means known to those of skill in the art. Methods for selection of appropriate epitopes, such as those near the C-terminus or in hydrophilic regions are well described in the art. (See, e.g., Ausubel supra, ch. 11.)

Typically, oligopeptides 15 residues in length are synthesized using an Applied Biosystems Peptide Synthesizer Model 431A using fmoc-chemistry and coupled to KLH (Sigma, St. Louis, Mo.) by reaction with N-maleimidobenzoyl-N-hydroxysuccinimide ester (MBS) to increase immunogenicity. (See, e.g., Ausubel supra.) Rabbits are immunized with the oligopeptide-KLH complex in complete Freund's adjuvant. Resulting antisera are tested for antipeptide activity by, for example, binding the peptide to plastic, blocking with 1% BSA, reacting with rabbit antisera, washing, and reacting with radio-iodinated goat anti-rabbit IgG.

XIII. Purification of Naturally Occurring hChk1 Using Specific Antibodies

Naturally occurring or recombinant hChk1 is substantially purified by immunoaffinity chromatography using antibodies specific for hChk1. An immunoaffinity column is constructed by covalently coupling anti-hChk1 antibody to an activated chromatographic resin, such as CNBr-activated Sepharose (Pharmacia & Upjohn). After the coupling, the resin is blocked and washed according to the manufacturer's instructions.

Media containing hChk1 are passed over the immunoaffinity column, and the column is washed under conditions that allow the preferential absorbance of hChk1 (e.g., high ionic strength buffers in the presence of detergent). The column is eluted under conditions that disrupt antibody/hChk1 binding (e.g., a buffer of pH 2 to pH 3, or a high concentration of a chaotrope, such as urea or thiocyanate ion), and hChk1 is collected.

XIV. Identification of Molecules which Interact with hChk1 hChk1, or biologically active fragments thereof, are labeled with $^{125}$I Bolton-Hunter reagent. (See, e.g., Bolton et al. (1973) Biochem. J. 133:529.) Candidate molecules previously arrayed in the wells of a multi-well plate are incubated with the labeled hChk1, washed, and any wells with labeled hChk1 complex are assayed. Data obtained using different concentrations of hChk1 are used to calculate values for the number, affinity, and association of hChk1 with the candidate molecules.

Various modifications and variations of the described methods and systems of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

TABLE 1

| Program | Description | Reference | Parameter Threshold |
|---|---|---|---|
| ABI FACTURA | A program that removes vector sequences and masks ambiguous bases in nucleic acid sequences. | Perkin-Elmer Applied Biosystems, Foster City, CA. | |
| ABI/PARACEL FDF | A Fast Data Finder useful in comparing and annotating amino acid or nucleic acid sequences. | Perkin-Elmer Applied Biosystems, Foster City, CA; Paracel Inc., Pasadena, CA. | Mismatch <50% |
| ABI AutoAssembler | A program that assembles nucleic acid sequences. | Perkin-Elmer Applied Biosystems, Foster City, CA. | |
| BLAST | A Basic Local Alignment Search Tool useful in sequence similarity search for amino acid and nucleic acid sequences. BLAST includes five functions: blastp, blastn, blastx, tblastn, and tblastx. | Altschul, S. F. et al. (1990) J. Mol. Biol. 215:403–410; Altschul, S. F. et al. (1997) Nucleic Acids Res. 25:3389–3402. | ESTs: Probability value = 1.0E−8 or less<br>Full Length sequences: Probability value = 1.0E−10 or less |
| FASTA | A Pearson and Lipman algorithm that searches for similarity between a query sequence and a group of sequences of the same type. FASTA comprises as least five functions: fasta, tfasta, fastx, tfastx, and ssearch. | Pearson, W. R. and D. J. Lipman (1988) Proc. Natl. Acad. Sci. 85:2444–2448; Pearson, W. R. (1990) Methods Enzymol. 183:63–98; and Smith, T. F. and M. S. Waterman (1981) Adv. Appl. Math. 2:482–489. | ESTs: fasta E value = 1.06E−6 Assembled ESTs: fasta Identity = 95% or greater and Match length = 200 bases or greater; fastx E value = 1.0E−8 or less<br>Full Length sequences: fastx score = 100 or greater |
| BLIMPS | A BLocks IMProved Searcher that matches a sequence against those in BLOCKS and PRINTS databases to search for gene families, sequence homology, and structural fingerprint regions. | Henikoff, S and J. G. Henikoff, Nucl. Acid Res., 19:6565–72, 1991. J. G. Henikoff and S. Henikoff (1996) Methods Enzymol. 266:88–105; and Attwood, T. K. et al. (1997) J. Chem. Inf. Comput. Sci. 37:417–424. | Score = 1000 or greater; Ratio of Score/Strength = 0.75 or larger; and Probability value = 1.0E−3 or less |
| PFAM | A Hidden Markov Models-based application useful for protein family search. | Krogh, A. et al. (1994) J. Mol. Biol., 235:1501–1531; Sonnhammer, E. L. L et al. (1988) Nucleic Acids Res. 26:320–322. | Score = 10–50 bits, depending on individual protein families |
| ProfileScan | An algorithm that searches for structural and sequence motifs in protein sequences that match sequence patterns defined in Prosite. | Gribskov, M. et al. (1988) CABIOS 4:61–66; Gribskov, et al. (1989) Methods Enzymol. 183:146–159; Bairoch, A. et al. (1997) Nucleic Acids Res. 25:217–221. | Score = 4.0 or greater |
| Phred | A base-calling algorithm that examines automated sequencer traces with high sensitivity and probability. | Ewing, B. et al. (1998) Genome Res. 8:175–185; Ewing, B. and P. Green (1998) Genome Res. 8:186–194. | |
| Phrap | A Phils Revised Assembly Program including SWAT and CrossMatch, programs based on efficient implementation of the Smith-Waterman algorithm, useful in searching sequence homology and assembling DNA sequences. | Smith, T. F. and M. S. Waterman (1981) Adv. Appl. Math. 2:482–489; Smith, T. F. and M. S. Waterman (1981) J. Mol. Biol. 147:195–197, and Green, P., University of Washington, Seattle, WA. | Score = 120 or greater; Match length = 56 or greater |
| Consed | A graphical tool for viewing and editing Phrap assemblies | Gordon, D. et al. (1998) Genome Res. 8:195–202. | |
| SPScan | A weight matrix analysis program that scans protein sequences for the presence of secretory signal peptides. | Nielson, H. et al. (1997) Protein Engineering 10:1–6; Claverie, J. M. and S. Audic (1997) CABIOS 12:431–439. | Score = 5 or greater |
| Motifs | A program that searches amino acid sequences for patterns that matched those defined in Prosite. | Bairoch et al. supra; Wisconsin Package Program Manual, version 9, page M51–59, Genetics Computer Group, Madison, WI. | |

What is claimed is:

1. An isolated and purified polynucleotide comprising the polynucleotide sequence of SEQ ID NO:2.

2. An isolated and purified polynucleotide variant of the polynucleotide of claim 1 comprising the polynucleotide sequence of SEQ ID NO:16.

3. An isolated and purified polynucleotide which is completely complementary to the polynucleotide of claim 1.

4. An expression vector comprising the polynucleotide of claim 1.

5. A host cell comprising the expression vector of claim 4.

6. A method for producing a polypeptide, the method comprising the steps of:

(a) culturing the host cell of claim 5, under conditions suitable for the expression of the polypeptide; and (b) recovering the polypeptide from the host cell culture.

7. A method for detecting a polynucleotide in a sample, the method comprising the steps of:

(a) hybridizing the polynucleotide of claim 3 to at least one nucleic acid in a sample, thereby forming a hybridization complex; and (b) detecting the hybridization complex, wherein the presence of the hybridization complex correlates with the presence of a polynucleotide in the sample.

8. The method of claim 7 further comprising amplifying the polynucleotide prior to hybridization.

9. An isolated and purified fragment of the polynucleotide of claim 1 selected from the group consisting of SEQ ID NO:4, SEQ ID NO:7, SEQ ID NO:9–11, and SEQ ID NO:13–14.

10. A method of using a polynucleotide to screen a library of molecules or compounds to identify at least one molecule or compound which specifically binds the polynucleotide, the method comprising:

a) combining the polynucleotide of claim 1 with the library of molecules or compounds under conditions to allow specific binding, and b) detecting specific binding, thereby identifying a molecule or compound which specifically binds the polynucleotide.

11. The method of claim 10 wherein the library is selected from DNA molecules, RNA molecules, PNAs, peptides, and chromosome constructions.

12. A method of using a polynucleotide to purify a molecule or compound which specifically binds the polynucleotide from a sample, the method comprising:

a) combining a polynucleotide of claim 1 with a sample under conditions to allow specific binding, b) recovering the bound polynucleotide, and c) separating the bound polynucleotide from the molecule or compound thereby obtaining the purified molecule or compound.

* * * * *

SEQUENCE LISTING

<160> NUMBER OF SEQ ID NOS: 16

<210> SEQ ID NO 1
<211> LENGTH: 476
<212> TYPE: PRT
<213> ORGANISM: HOMO SAPIENS
<220> FEATURE:
<223> OTHER INFORMATION: 516219, MMLR1DT01

<400> SEQUENCE: 1

```
Met Ala Val Pro Phe Val Glu Asp Trp Asp L eu Val Gln Thr Leu Gly
 1               5                  10                   15

Glu Gly Ala Tyr Gly Glu Val Gln Leu Ala V al Asn Arg Val Thr Glu
            20                  25                   30

Glu Ala Val Ala Val Lys Ile Val Asp Met L ys Arg Ala Val Asp Cys
        35                  40                  45

Pro Glu Asn Ile Lys Lys Glu Ile Cys Ile A sn Lys Met Leu Asn His
    50                  55                  60

Glu Asn Val Val Lys Phe Tyr Gly His Arg A rg Glu Gly Asn Ile Gln
65                  70                  75                      80

Tyr Leu Phe Leu Glu Tyr Cys Ser Gly Gly G lu Leu Phe Asp Arg Ile
                85                  90                   95

Glu Pro Asp Ile Gly Met Pro Glu Pro Asp A la Gln Arg Phe His
            100                 105                  110

Gln Leu Met Ala Gly Val Val Tyr Leu His G ly Ile Gly Ile Thr His
        115                 120                 125

Arg Asp Ile Lys Pro Glu Asn Leu Leu Leu A sp Glu Arg Asp Asn Leu
    130                 135                 140

Lys Ile Ser Asp Phe Gly Leu Ala Thr Val P he Arg Tyr Asn Asn Arg
145                 150                 155                    160

Glu Arg Leu Leu Asn Lys Met Cys Gly Thr L eu Pro Tyr Val Ala Pro
                165                 170                 175

Glu Leu Leu Lys Arg Arg Glu Phe His Ala G lu Pro Val Asp Val Trp
            180                 185                 190

Ser Cys Gly Ile Val Leu Thr Ala Met Leu A la Gly Glu Leu Pro Trp
        195                 200                 205

Asp Gln Pro Ser Asp Ser Cys Gln Glu Tyr S er Asp Trp Lys Glu Lys
    210                 215                 220

Lys Thr Tyr Leu Asn Pro Trp Lys Lys Ile A sp Ser Ala Pro Leu Ala
225                 230                 235                    240

Leu Leu His Lys Ile Leu Val Glu Asn Pro S er Ala Arg Ile Thr Ile
                245                 250                 255

Pro Asp Ile Lys Lys Asp Arg Trp Tyr Asn L ys Pro Leu Lys Lys Gly
            260                 265                 270

Ala Lys Arg Pro Arg Val Thr Ser Gly Gly V al Ser Glu Ser Pro Ser
        275                 280                 285

Gly Phe Ser Lys His Ile Gln Ser Asn Leu A sp Phe Ser Pro Val Asn
    290                 295                 300

Ser Ala Ser Ser Glu Glu Asn Val Lys Tyr S er Ser Ser Gln Pro Glu
305                 310                 315                    320

Pro Arg Thr Gly Leu Ser Leu Trp Asp Thr S er Pro Ser Tyr Ile Asp
                325                 330                 335

Lys Leu Val Gln Gly Ile Ser Phe Ser Gln P ro Thr Cys Pro Asp His
            340                 345                 350
```

```
Met Leu Leu Asn Ser Gln Leu Leu Gly Thr Pro Gly Ser Ser Gln Asn
            355                 360                 365

Pro Trp Gln Arg Leu Val Lys Arg Met Thr Arg Phe Phe Thr Lys Leu
    370                 375                 380

Asp Ala Asp Lys Ser Tyr Gln Cys Leu Lys Glu Thr Cys Glu Lys Leu
385                 390                 395                 400

Gly Tyr Gln Trp Lys Lys Ser Cys Met Asn Gln Val Thr Ile Ser Thr
                405                 410                 415

Thr Asp Arg Arg Asn Asn Lys Leu Ile Phe Lys Val Asn Leu Leu Glu
            420                 425                 430

Met Asp Asp Lys Ile Leu Val Asp Phe Arg Leu Ser Lys Gly Asp Gly
            435                 440                 445

Leu Glu Phe Lys Arg His Phe Leu Lys Ile Lys Gly Lys Leu Ile Asp
    450                 455                 460

Ile Val Ser Ser Gln Lys Val Trp Leu Pro Ala Thr
465                 470                 475
```

<210> SEQ ID NO 2
<211> LENGTH: 1479
<212> TYPE: DNA
<213> ORGANISM: HOMO SAPIENS
<220> FEATURE:
<223> OTHER INFORMATION: 516219, MMLR1DT01

<400> SEQUENCE: 2

```
gaattcggct tccaccatgg cagtgccctt tgtggaagac tgggacttgg tgcaaaccct    60
gggagaaggt gcctatggag aagttcaact tgctgtgaat agagtaactg aagaagcagt   120
cgcagtgaag attgtagata tgaagcgtgc cgtagactgt ccagaaaata ttaagaaaga   180
gatctgtatc aataaaatgc taaatcatga aatgtagta aaattctatg gtcacaggag   240
agaaggcaat atccaatatt tatttctgga gtactgtagt ggaggagagc ttttgacag    300
aatagagcca gacataggca tgcctgaacc agatgctcag agattcttcc atcaactcat   360
ggcagggtg gtttatctgc atggtattgg aataactcac agggatatta accagaaaa    420
tcttctgttg gatgaaaggg ataaccctcaa atctcagac tttggcttgg caacagtatt   480
tcggtataat aatcgtgagc gtttgttgaa caagatgtgt ggtactttac catatgttgc   540
tccagaactt ctgaagagaa gagaatttca tgcagaacca gttgatgttt ggtcctgtgg   600
aatagtactt actgcaatgc tcgctggaga attgccatgg gaccaaccca gtgacagctg   660
tcaggagtat tctgactgga agaaaaaaaa acatacctc aacccttgga aaaaatcga    720
ttctgctcct ctagctctgc tgcataaaat cttagttgag aatccatcag caagaattac   780
cattccagac atcaaaaaag atagatggta caacaaaccc tcaagaaag gggcaaaaag   840
gccccgagtc acttcaggtg gtgtgtcaga gtctcccagt ggattttcta agcacattca   900
atccaatttg gacttctctc cagtaaacag tgcttctagt gaagaaatgt gaagtactc    960
cagttctcag ccagaaccc gcacaggtct ttccttatgg gataccagcc ctcatacat   1020
tgataaattg gtacaaggga tcagcttttc ccagcccaca tgtcctgatc atatgctttt  1080
gaatagtcag ttacttggca ccccaggatc ctcacagaac ccctggcagc ggttggtcaa  1140
agaatgaca cgattcttta ccaaattgga tgcagacaaa tcttatcaat gcctgaaag   1200
gacttgtgag aagttgggct atcaatgaa gaaaagttgt atgaatcagg ttactatac   1260
aacaactgat aggagaaaca ataaactcat tttcaaagtg aatttgttag aatggagat    1320
taaatattg gttgacttcc ggcttttctaa gggtgatgga ttggagttca agagaccctt  1380
```

```
cctgaagatt aaagggaagc tgattgatat tgtgagcagc cagaaggttt g gcttctgc    1440 cacatgatcg gaccatcggc tctggggaat cctcgagtg                            1479
```

<210> SEQ ID NO 3
<211> LENGTH: 496
<212> TYPE: PRT
<213> ORGANISM: HOMO SAPIENS
<220> FEATURE:
<223> OTHER INFORMATION: 311176, GenBank

<400> SEQUENCE: 3

```
Met Ala Gln Lys Leu Asp Asn Phe Pro Tyr H is Ile Gly Arg Glu Ile
  1               5                  10                  15

Gly Thr Gly Ala Phe Ala Ser Val Arg Leu C ys Tyr Asp Asp Asn Ala
             20                  25                  30

Lys Ile Tyr Ala Val Lys Phe Val Asn Lys L ys His Ala Thr Ser Cys
         35                  40                  45

Met Asn Ala Gly Val Trp Ala Arg Arg Met A la Ser Glu Ile Gln Leu
     50                  55                  60

His Lys Leu Cys Asn Gly His Lys Asn Ile I le His Phe Tyr Asn Thr
 65                  70                  75                  80

Ala Glu Asn Pro Gln Trp Arg Trp Val Val L eu Glu Phe Ala Gln Gly
                 85                  90                  95

Gly Asp Leu Phe Asp Lys Ile Glu Pro Asp V al Gly Ile Asp Glu Asp
            100                 105                 110

Val Ala Gln Phe Tyr Phe Ala Gln Leu Met G lu Gly Ile Ser Phe Met
        115                 120                 125

His Ser Lys Gly Val Ala His Arg Asp Leu L ys Pro Glu Asn Ile Leu
    130                 135                 140

Leu Asp Tyr Asn Gly Asn Leu Lys Ile Ser A sp Phe Gly Phe Ala Ser
145                 150                 155                 160

Leu Phe Ser Tyr Lys Gly Lys Ser Arg Leu L eu Asn Ser Pro Val Gly
                165                 170                 175

Ser Pro Pro Tyr Ala Ala Pro Glu Ile Thr G ln Gln Tyr Asp Gly Ser
            180                 185                 190

Lys Val Asp Val Trp Ser Cys Gly Ile Ile L eu Phe Ala Leu Leu Leu
        195                 200                 205

Gly Asn Thr Pro Trp Asp Glu Ala Ile Ser A sn Thr Gly Asp Tyr Leu
    210                 215                 220

Leu Tyr Lys Lys Gln Cys Glu Arg Pro Ser T yr His Pro Trp Asn Leu
225                 230                 235                 240

Leu Ser Pro Gly Ala Tyr Ser Ile Ile Thr G ly Met Leu Arg Ser Asp
                245                 250                 255

Pro Phe Lys Arg Tyr Ser Val Lys His Val V al Gln His Pro Trp Leu
            260                 265                 270

Thr Ser Ser Thr Pro Phe Arg Thr Lys Asn G ly Asn Cys Ala Asp Pro
        275                 280                 285

Val Ala Leu Ala Ser Arg Leu Met Lys Leu A rg Ile Asp Leu Asp
    290                 295                 300

Lys Pro Arg Leu Ala Ser Ser Arg Ala Ser G ln Asn Asp Ser Gly Phe
305                 310                 315                 320

Ser Met Thr Gln Pro Ala Phe Lys Lys Asn A sp Gln Lys Glu Leu Asp
                325                 330                 335

Arg Val Glu Val Tyr Gly Ala Leu Ser Gln P ro Val Gln Leu Asn Lys
            340                 345                 350
```

```
Asn Ile Asp Val Thr Glu Ile Leu Glu Lys Asp Pro Ser Leu Ser Gln
            355                 360                 365

Phe Cys Glu Asn Glu Gly Phe Ile Lys Arg Leu Ala Lys Lys Ala Lys
370                 375                 380

Asn Phe Tyr Glu Ile Cys Pro Pro Glu Arg Leu Thr Arg Phe Tyr Ser
385                 390                 395                 400

Arg Ala Ser Arg Glu Thr Ile Ile Asp His Leu Tyr Asp Ser Leu Arg
                405                 410                 415

Leu Leu Ala Ile Ser Val Thr Met Lys Tyr Val Arg Asn Gln Thr Ile
            420                 425                 430

Leu Tyr Val Asn Leu His Asp Lys Arg Lys Cys Leu Leu Gln Gly Val
            435                 440                 445

Ile Glu Leu Thr Asn Leu Gly His Asn Leu Glu Leu Ile Asn Phe Ile
    450                 455                 460

Lys Arg Asn Gly Asp Pro Leu Glu Trp Arg Lys Phe Phe Lys Asn Val
465                 470                 475                 480

Val Ser Ser Ile Gly Lys Pro Ile Val Leu Thr Asp Val Ser Gln Asn
            485                 490                 495
```

<210> SEQ ID NO 4
<211> LENGTH: 235
<212> TYPE: DNA
<213> ORGANISM: HOMO SAPIENS
<220> FEATURE:
<221> NAME/KEY: unsure
<222> LOCATION: 44, 51, 63, 82, 129, 153, 161, 197, 199, 200, 217, 224,
      231
<223> OTHER INFORMATION: a or g or c or t, unknown, or other
<220> FEATURE:
<223> OTHER INFORMATION: 046081H1, CORNNOT01

<400> SEQUENCE: 4

```
gcaaggaca gtccgccgag gtgctcggtg gagtcatggc attnccttt n tggaagact    60 ggnccttggt gcaaaccctg gnagaaggtg cctatggaga agttcaactt g ctgtaaata   120 gagtaactna agaagcagtc gcagtgaaga ttntagatat naagcgtgcc g tagactgtc   180 ccgaaaatat taagtangnn atctgtatca ataaaantgc taantcatga n aatt       235
```

<210> SEQ ID NO 5
<211> LENGTH: 342
<212> TYPE: DNA
<213> ORGANISM: HOMO SAPIENS
<220> FEATURE:
<221> NAME/KEY: unsure
<222> LOCATION: 26, 48, 59, 69, 98, 166, 169, 200, 221, 224, 227, 231,
      240,
<222> LOCATION: 241,242, 247, 251, 252, 257, 260, 267, 284, 292, 296,
      303,
<222> LOCATION: 305, 306, 319, 337, 339
<223> OTHER INFORMATION: a or g or c or t, unknown, or other
<220> FEATURE:
<223> OTHER INFORMATION: 046081F1, CORNNOT01

<400> SEQUENCE: 5

```
gccccaaagt tgatacaatt ttattngaaa accaacttt tgtaagtnta a caggtaang    60 gaccaaggnt cagtctattt tcttatagtt ccttactntt ccttcctctt t attcttata   120 cctaaagttt gtcaccagta gttgaaaggt aaatatggtt tgaagnggna a tttgggaaa   180 tttttagggt gttcaaaggn attttttggg aaagttggta ngncctnggg n tttgcaacn   240 nntaagncaa ngnttttnctn cctccantgg gaaacacctt cttnaatttt a nttancatt   300 ttntnnaaac cgggtttttnt tcctggcccg gcccttngng tt                      342
```

-continued

<210> SEQ ID NO 6
<211> LENGTH: 863
<212> TYPE: DNA
<213> ORGANISM: HOMO SAPIENS
<220> FEATURE:
<221> NAME/KEY: unsure
<222> LOCATION: 3, 13, 17, 21, 27, 31, 85 , 89, 103, 117, 142, 165, 167, 171, 175,
<222> LOCATION: 229, 266, 274, 287, 288, 307 , 326, 403, 502, 533, 544, 546, 551,
<222> LOCATION: 562, 563, 569, 594, 605, 643 , 652, 655, 671, 688, 689, 706, 708,
<222> LOCATION: 711, 719, 721, 731, 736, 741 , 749, 751, 755, 756, 758, 760, 772,
<222> LOCATION: 775, 779, 780, 786, 787, 788 , 794, 796, 804, 808, 813, 825, 829,
<222> LOCATION: 830, 836, 838, 841, 849, 858 , 860
<223> OTHER INFORMATION: a or g or c or t, unknown, or other
<220> FEATURE:
<223> OTHER INFORMATION: 046081X3, CORNNOT01

<400> SEQUENCE: 6

```
ctnggtcaat ctnaagncga ngggccnggc nccacatgga aatgttttttt t ttgaagact      60
gggacttggt gcaaacccgg ggagnaggnc cctaagaaaa aancagtcgc a gtgaanatt     120
gtagatatga agcgtgccgt anactgtcca gaaaatatta agaantntat n tttntcaat     180
aaaatgctaa atcatgaaaa tgtagtaaaa ttctatggtc acaggagana a ggcaatatc     240
caatatttat ttctggagta ctgtantgga gganagcttt ttgaccnncc c gagccagac     300
ataggcntgc ctgaaccaaa tgctcntata ttcttccatc aactcatggc a gggtggtt     360
tatctgcatg gtattggaat aactcacagg gatattaaac canaaaaatc t tctgttgga     420
tgaaagggat aacctcaaaa tctcagactt tggcttggca acagtatttc g gtataataa     480
tcgtgagcgt ttgttgaaca anatgtgtgg tactttacca tatgttgctc c anaacttct     540
gaananaaaa naattccatg cnnaaccant ttgatgtttg gtcctgtgga a tantactta     600
ctgcnatgct cgctggagaa ttgccatggg accaacccac ganagctgtc a ngantattc     660
tgactggaaa naaaaaaaaa catactcnnc ccttggaaaa aaatcnantc n gctcctcna     720
nctctgccgc ntaaanccta nttgaaatnc ntccnncnan aataccttcc c naantccnn     780
aaaaannntg gtcncncccc ccanaaangg ggnaaaggcc caatnccntn g gtgtntntc     840
naatccccnt ggattccnan cac                                             863
```

<210> SEQ ID NO 7
<211> LENGTH: 218
<212> TYPE: DNA
<213> ORGANISM: HOMO SAPIENS
<220> FEATURE:
<221> NAME/KEY: unsure
<222> LOCATION: 27, 50, 172
<223> OTHER INFORMATION: a or g or c or t, unknown, or other
<220> FEATURE:
<223> OTHER INFORMATION: 516219H1, MMLR1DT01

<400> SEQUENCE: 7

```
cttctgttgg atgaaaggga taacctnaaa atctcagact ttggcttggn a acagtattt     60
cggtataata atcgtgagcg tttgttgaac aagatgtgtg gtactttacc a tatgttgct    120
ccagaacttc tgaagagaag agatttcatg cagaaccagt tgatgtttgg t nctgtggaa    180
tagtacttac tgcaatgctc gctggagaat tgccatgg                              218
```

<210> SEQ ID NO 8
<211> LENGTH: 323
<212> TYPE: DNA

```
<213> ORGANISM: HOMO SAPIENS
<220> FEATURE:
<221> NAME/KEY: unsure
<222> LOCATION: 255, 263, 319, 321
<223> OTHER INFORMATION: a or g or c or t, unknown, or other
<220> FEATURE:
<223> OTHER INFORMATION: 516219F1, MMLR1DT01

<400> SEQUENCE: 8
aggattcccc agagccgatg gtccgatcat gtggcaggaa gccaaacctt c tggctgctc      60 acatatcaat cagcttccct ttaatcttca ggaagtgtct cttgaactcc a atccatcac     120 ccttagaaag ccggaagtca accaatattt tatcatccat ttctaacaaa t tcactttga     180 aaatgagttt attgtttctc ctatcagttg ttgatatagt aacctgattc a tacaacttt     240 tcttccattg atagnccaac ttntcacaag tctctttcag gcattgatag g tttgtctgc     300 atccatttgg taaaggatng ngt                                              323

<210> SEQ ID NO 9
<211> LENGTH: 519
<212> TYPE: DNA
<213> ORGANISM: HOMO SAPIENS
<220> FEATURE:
<221> NAME/KEY: unsure
<222> LOCATION: 3, 11, 25, 216, 242, 363, 364, 399, 431, 499, 515, 516
<223> OTHER INFORMATION: a or g or c or t, unknown, or other
<220> FEATURE:
<223> OTHER INFORMATION: 516219X5, MMLR1DT01

<400> SEQUENCE: 9
tanaggcaaa ngacagtccc cccangtgct tggtggagtc atggcagtgc c ctttgtgga      60 agactgggac ttggtgcaaa ccctgggaga aggtgcctat ggagaagttc a acttgctgt    120 gaatagagta actgaagaag cagtcgcagt gaagattgta gatatgaagc g tgccgtaga    180 ctgtccagaa aatattaaga aagagatctg tatcantaaa atgctaaatc a tgaaaatgt    240 antaaaattc tatggtcaca ggagagaagg caatatccaa tatttatttc t ggagtactg    300 tagtggagga gagcttttg acagaataga gccagacata ggcatgcctg a accagatgc    360 tcnnagattc ttccatcaac tcatggcagg ggtggtttnt ctgcatggta t tggaataac    420 tcacgggat nttaaaccag aaaatcttct gttggatgaa agggataacc t caaaatctc    480 agactttggc ttggcaacng tatttcggta taatnnggg                            519

<210> SEQ ID NO 10
<211> LENGTH: 357
<212> TYPE: DNA
<213> ORGANISM: HOMO SAPIENS
<220> FEATURE:
<221> NAME/KEY: unsure
<222> LOCATION: 46
<223> OTHER INFORMATION: a or g or c or t, unknown, or other
<220> FEATURE:
<223> OTHER INFORMATION: 2044650H1, THP1T7T01

<400> SEQUENCE: 10
ggggtttaat atccctgtga gttattccaa taccatgcag ataaancacc c ctgccatga     60 gttgatggaa gaatctctga gcatctggtt caggcatgcc tatgtctggc t ctattctgt   120 caaaaagctc tcctccacta cagtactcca gaaataaata ttggatattg c cttctctcc   180 tgtgaccata gaatttttact acatttttcat gatttagcat tttattgata c agatctctt   240 tcttaatatt ttctggacag tctacggcac gcttcatatc tacaatcttc a ctgcgactg   300 ttcttcagtt actctattca cagcaagttg aattctccca taggcacctc g agccgg      357
```

<210> SEQ ID NO 11
<211> LENGTH: 286
<212> TYPE: DNA
<213> ORGANISM: HOMO SAPIENS
<220> FEATURE:
<221> NAME/KEY: unsure
<222> LOCATION: 45, 49, 58, 59, 62, 63, 6 6, 68
<223> OTHER INFORMATION: a or g or c or t, unknown, or other
<220> FEATURE:
<223> OTHER INFORMATION: 2731758H1, OVARTUT04

<400> SEQUENCE: 11

```
tgcatttgga ttcctgcagt ggtgggcaaa ggacagtccg ccgangtgnt c ggtggannc      60
cnnggnantg ccctttgtgg aagactggga cttggtgcaa accctgggag a aggtgccta     120
tggagaagtt caacttgctg tgaatagagt aactgaagaa gcagtcgcag t gaagattgt     180
agatatgaag cgtgccgtag actgtccaga aaatattaag aaagagatct g tatcaataa    240
aatgctaaat catgaaaatg tagtaaaatt ctatggtcac aggaga                    286
```

<210> SEQ ID NO 12
<211> LENGTH: 22
<212> TYPE: PRT
<213> ORGANISM: HOMO SAPIENS

<400> SEQUENCE: 12

```
Cys Gly Lys Ile Lys Gly Lys Leu Ile Asp I le Val Ser Ser Gln Lys
  1               5                  10                  15

Val Trp Leu Pro Ala Thr
            20
```

<210> SEQ ID NO 13
<211> LENGTH: 87
<212> TYPE: DNA
<213> ORGANISM: HOMO SAPIENS

<400> SEQUENCE: 13

```
gtgaattcac caccatggca gtgccctttg tggaagactg ggacttggtg c aaaccctgg      60
gagaaggtgc ctatggagaa gttcaac                                          87
```

<210> SEQ ID NO 14
<211> LENGTH: 29
<212> TYPE: DNA
<213> ORGANISM: HOMO SAPIENS

<400> SEQUENCE: 14

```
cactcgagga ttccccagag ccgatggtc                                        29
```

<210> SEQ ID NO 15
<211> LENGTH: 57
<212> TYPE: DNA
<213> ORGANISM: HOMO SAPIENS

<400> SEQUENCE: 15

```
ggataactc acagggatat taaaccagaa aatcttctgt tggatgaaag g gataac          57
```

<210> SEQ ID NO 16
<211> LENGTH: 1479
<212> TYPE: DNA
<213> ORGANISM: HOMO SAPIENS

-continued

```
<400> SEQUENCE: 16
gaattcggct tccaccatgg cagtgccctt tgtggaagac tgggacttgg t gcaaaccct      60 gggagaaggt gcctatggag aagttcaact tgctgtgaat agagtaactg a agaagcagt     120 cgcagtggcg attgtagata tgaagcgtgc cgtagactgt ccagaaaata t taagaaaga    180 gatctgtatc aataaaatgc taatcatga aaatgtagta aaattctatg g tcacaggag     240 agaaggcaat atccaatatt tatttctgga gtactgtagt ggaggagagc t ttttgacag    300 aatagagcca gacataggca tgcctgaacc agatgctcag agattcttcc a tcaactcat    360 ggcagggtg gtttatctgc atggtattgg aataactcac agggatatta a accagaaaa    420 tcttctgttg gatgaaaggg ataacctcaa aatctcagac tttggcttgg c aacagtatt   480 tcggtataat aatcgtgagc gtttgttgaa caagatgtgt ggtactttac c atatgttgc    540 tccagaactt ctgaagagaa gagaatttca tgcagaacca gttgatgttt g gtcctgtgg   600 aatagtactt actgcaatgc tcgctggaga attgccatgg gaccaaccca g tgacagctg   660 tcaggagtat tctgactgga aagaaaaaaa aacatacctc aacccttgga a aaaaatcga   720 ttctgctcct ctagctctgc tgcataaaat cttagttgag aatccatcag c aagaattac   780 cattccagac atcaaaaaag atagatggta caacaaaccc ctcaagaaag g ggcaaaaag   840 gccccgagtc acttcaggtg gtgtgtcaga gtctcccagt ggattttcta a gcacattca   900 atccaatttg gacttctctc cagtaaacag tgcttctagt gaagaaaatg t gaagtactc   960 cagttctcag ccagaacccc gcacaggtct ttccttatgg gataccagcc c ctcatacat  1020 tgataaattg gtacaaggga tcagcttttc ccagcccaca tgtcctgatc a tatgctttt  1080 gaatagtcag ttacttggca ccccaggatc ctcacagaac ccctggcagc g gttggtcaa  1140 aagaatgaca cgattcttta ccaaattgga tgcagacaaa tcttatcaat g cctgaaaga  1200 gacttgtgag aagttgggct atcaatggaa gaaaagttgt atgaatcagg t tactatatc  1260 aacaactgat aggagaaaca ataaactcat tttcaaagtg aatttgttag a aatggatga  1320 taaaatattg gttgacttcc ggctttctaa gggtgatgga ttggagttca a gagacactt  1380 cctgaagatt aaagggaagc tgattgatat tgtgagcagc cagaaggttt g gcttcctgc  1440 cacatgatcg gaccatcggc tctggggaat cctcgagtg                            1479
```